(12) United States Patent
Rubinstein et al.

(10) Patent No.: US 8,337,444 B2
(45) Date of Patent: Dec. 25, 2012

(54) MEASUREMENT OF CARDIAC OUTPUT AND BLOOD VOLUME BY NON-INVASIVE DETECTION OF INDICATOR DILUTION FOR HEMODIALYSIS

(75) Inventors: Eduardo H. Rubinstein, Los Angeles, CA (US); Daniel P. Holschneider, Los Angeles, CA (US); Jean-Michel I. Maarek, Rancho Palos Verdes, CA (US)

(73) Assignee: Alfred E. Mann Institute for Biomedical Engineering at the University of Southern California, Los Angeles, CA (US)

( * ) Notice: Subject to any disclaimer, the term of this patent is extended or adjusted under 35 U.S.C. 154(b) by 1151 days.

(21) Appl. No.: 11/744,157

(22) Filed: May 3, 2007

(65) Prior Publication Data

US 2008/0015434 A1 Jan. 17, 2008

Related U.S. Application Data

(63) Continuation-in-part of application No. 10/847,480, filed on May 17, 2004, now Pat. No. 7,590,437, which is a continuation of application No. 10/153,387, filed on May 21, 2002, now Pat. No. 6,757,554.

(60) Provisional application No. 60/747,464, filed on May 17, 2006, provisional application No. 60/292,580, filed on May 22, 2001.

(51) Int. Cl.
*A61M 37/00* (2006.01)
*A61B 6/00* (2006.01)
*A61B 5/02* (2006.01)

(52) U.S. Cl. ....... 604/6.08; 604/4.01; 600/431; 600/526

(58) Field of Classification Search ........ 600/4.01–6.16, 600/65–67, 317, 322, 431, 526; 356/442; 128/633–635, 664–667; 422/44–48; 604/4.01–6.16, 604/65–67

See application file for complete search history.

(56) References Cited

U.S. PATENT DOCUMENTS

| | | | |
|---|---|---|---|
| 4,109,647 A | 8/1978 | Stern et al. | |
| 4,303,336 A | 12/1981 | Cullis | |
| 4,730,622 A | 3/1988 | Cohen | |
| 5,217,456 A | 6/1993 | Narciso, Jr. | |
| 5,331,958 A * | 7/1994 | Oppenheimer | ............... 600/322 |

(Continued)

FOREIGN PATENT DOCUMENTS

EP 0720013 7/1996

(Continued)

OTHER PUBLICATIONS

Darovic, G.O. Hemodynamic monitoring. Chapter 11: Monitoring cardiac output. 1995. pp. 327-346. 2d Ed. W.B. Saunders.

(Continued)

*Primary Examiner* — Philip R Wiest
(74) *Attorney, Agent, or Firm* — McDermott Will & Emery LLP

(57) ABSTRACT

A system and method of non-invasive or minimally invasive evaluating the cardiovascular system parameters to estimate the cardiac output and circulating blood volume of a patient undergoing hemodialysis. Intravascular indicators are stimulated, and emissions patterns detected for computation of cardiac output, cardiac index, blood volume and other indicators of cardiovascular health before and during hemodialysis.

24 Claims, 19 Drawing Sheets

U.S. PATENT DOCUMENTS

| | | | |
|---|---|---|---|
| 5,601,080 A * | 2/1997 | Oppenheimer | 600/322 |
| 5,685,989 A | 11/1997 | Krivitski et al. | |
| 5,687,726 A | 11/1997 | Hoeft | |
| 5,766,125 A | 6/1998 | Aoyagi et al. | |
| 5,797,396 A | 8/1998 | Geiser et al. | |
| 5,830,365 A | 11/1998 | Schneditz | |
| 5,928,625 A * | 7/1999 | Dorshow et al. | 424/9.1 |
| 5,999,841 A | 12/1999 | Aoyagi et al. | |
| 6,041,246 A | 3/2000 | Krivitski et al. | |
| 6,061,590 A | 5/2000 | Krivitski | |
| 6,159,445 A | 12/2000 | Klaveness et al. | |
| 6,178,340 B1 | 1/2001 | Svetliza | |
| 6,219,566 B1 * | 4/2001 | Weersink et al. | 600/317 |
| 6,223,069 B1 | 4/2001 | Pfeiffer et al. | |
| 6,228,344 B1 | 5/2001 | Donshow et al. | |
| 6,230,035 B1 | 5/2001 | Aoyagi et al. | |
| 6,280,386 B1 | 8/2001 | Alfano et al. | |
| 6,280,703 B1 | 8/2001 | Combs et al. | |
| 6,299,583 B1 | 10/2001 | Eggers et al. | |
| 6,424,857 B1 | 7/2002 | Henrichs et al. | |
| 6,493,567 B1 * | 12/2002 | Krivitski et al. | 600/322 |
| 6,542,769 B2 | 4/2003 | Schwamm et al. | |
| 6,554,775 B1 | 4/2003 | Peyman et al. | |
| 6,718,190 B2 | 4/2004 | Krivitski et al. | |
| 6,746,407 B2 | 6/2004 | Steuer et al. | |
| 6,746,408 B2 | 6/2004 | Krivitski et al. | |
| 6,746,415 B1 | 6/2004 | Steuer et al. | |
| 6,756,554 B1 | 6/2004 | Rubinstein et al. | |
| 6,986,744 B1 | 1/2006 | Krivitski | |
| 7,261,696 B2 | 8/2007 | Krivitski | |
| 2002/0151774 A1 | 10/2002 | Soller et al. | |
| 2003/0113931 A1 | 6/2003 | Pan et al. | |
| 2004/0156782 A1 | 8/2004 | Alum et al. | |

FOREIGN PATENT DOCUMENTS

| | | |
|---|---|---|
| WO | WO 2006/039731 A1 | 4/2006 |
| WO | 2007/136521 | 11/2007 |

OTHER PUBLICATIONS

Desmettre, T. et al. Fluorescence properties and metabolic features of indocyanine green (ICG) as related to angiography. Survey of opthalmology. Jul.-Aug. 2000. pp. 15-27. vol. 45, No. 1.

Diamond, et al. Quantification of fluorophore concentration in tissue-simulating media by fluorescence measurements with a single optical fiber. Applied Optics, vol. 42, No. 13, May 2003, pp. 2436-2442.

Dorshow. R.B. et al. Noninvasive fluorescence detection of hepatic and renal function. Journal of biomedical optics. Jul. 1998. pp. 340-345. vol. 3, No. 3.

Edwards, A.D. et al. Measurement of hemoglobin flow and blood flow by near-infrared spectroscopy. J. Applied Physiology, 1993, vol. 75, pp. 1884-1889.

Fok et al. Oxygen consumption by lungs with acute and chronic injury in a rabbit model. Intensive care medicine. 2001. pp. 1532-1538. vol. 27.

Geddes, L.A. Cardiovascular devices and their applications. Chapter 4: The measurement of cardiac output and blood flow. 1984. pp. 101-120. John Wiley & Sons, New York.

Hollins, B. et al. Fluorometric determination of indocyanine green in plasma. Clinical chemistry. 1987. pp. 765-768. vol. 33, No. 6.

Iijima T. et al. Cardiac output and circulating blood vol. analysis by pulse dye densitometry. Journal of Clinical Monitoring, vol. 13, pp. 81-89, 1997.

Nihon Kohden. website: http://kohden.co.jp/intl/ppms-ddg2001.html. Website viewed May 17, 2001.

Preckel, B. et al. Effect of dantrolene in an in vivo and in vitro model of myocardial reperfusion injury. Acta Anaesthesiol Scand. 2000. pp. 194-201. vol. 44.

Sakka, G. et al. Comparison of Cardiac Output and Circulatory Blood Volumes By Transpulmonary Thermo-dye Dilution and Transcutaneous Indocyanine Green Measurement in Critically Ill Patients. Feb. 2002. pp. 559-565.Chest vol.121, No. 2.

Wang, L. et al. MCML—Monte Carlo modeling of light transport in multi-layered tissues. Computer Methods & Programs in Biomedicine, vol. 47, No. 2, pp. 131-146, 1995.

Weersink at al. Noninvasive measurement of fluorophore concentration in turbid media with a simple fluorescence/reflectance ratio technique. Applied Optics, vol. 40, No. 34, Dec. 2001, pp. 6389-6395.

De Vries, J-P. P.M. et al. 1992. Continuous Measurement of Blood Volume During Hemodialysis by an Optical Method. In 4535 ASAIO Transactions, ASAIO Journal, Jul.-Sep. 1992, vol. 38, No. 3, pp. M181-M185.

Extended European Search Report, dated Jul. 29, 2010, for European Patent Application No. 07794533.5 (European counterpart to U.S. Appl. No. 11/744,157, and regional phase of PCT/US2007/010786).

* cited by examiner

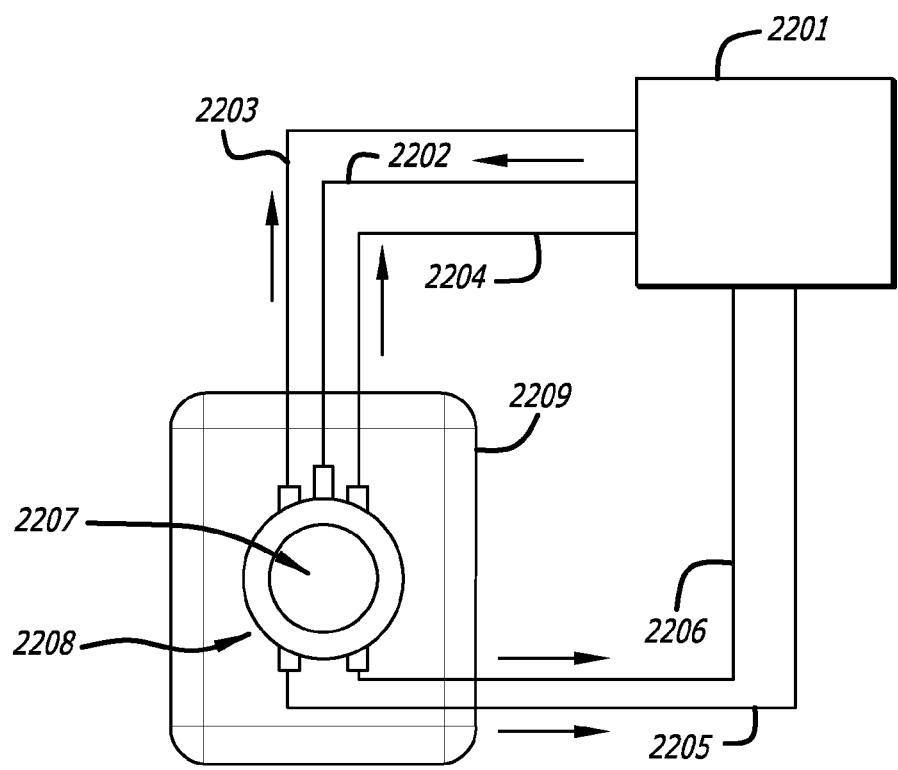
FIG. 22A
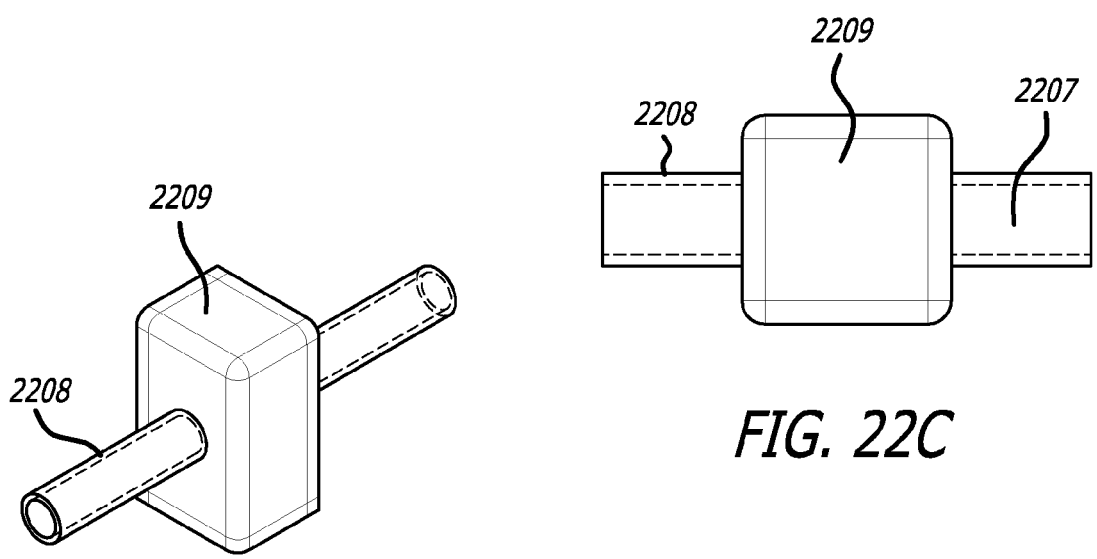
FIG. 22B
FIG. 22C

MEASUREMENT OF CARDIAC OUTPUT AND BLOOD VOLUME BY NON-INVASIVE DETECTION OF INDICATOR DILUTION FOR HEMODIALYSIS

CROSS-REFERENCE TO RELATED APPLICATIONS

This application claims the benefit of an earlier-filed U.S. Provisional Patent Application Ser. No. 60/747,464, filed May 17, 2006, entitled "Measurement of Cardiac Output and Blood Volume by Non-Invasive Detection of Indicator Dilution for Hemodialysis,". This application is also a continuation-in-part of U.S. patent application Ser. No. 10/847,480, filed May 17, 2004 now U.S. Pat. No. 7,590,437, entitled "Measurement of Cardiac Output and Blood Volume by Non-Invasive Detection of Indicator Dilution,"; which is Continuation of U.S. patent application Ser. No. 10/153,387, filed May 21, 2002 (now U.S. Pat. No. 6,757,554, issued Jun. 29, 2004) entitled "Measurement of Cardiac Output and Blood Volume by Non-Invasive Detection of Indicator Dilution,"; which claims priority to U.S. Provisional Application No. 60/292,580, filed May 22, 2001, entitled "Method and Apparatus for Measurement of Cardiac Output and Blood Volume by Noninvasive Detection of Indicator Dilution,". This application is also related to U.S. patent application Ser. No. 11/625,184, filed Jan. 19, 2007, entitled "Measurement of Cardiac Output and Blood Volume by Non-Invasive Detection of Indicator Dilution". The content of all of these applications is incorporated herein by reference.

1. FIELD

This application pertains to the detection of parameters of cardiovascular system of a subject.

2. GENERAL BACKGROUND AND STATE OF THE ART

Cardiac output is a central part of the hemodynamic assessment in patients having heart disease, acute hemodynamic compromise or undergoing cardiac surgery, for example. Cardiac output is a measure of the heart's effectiveness at circulating blood throughout the circulatory system. Specifically, cardiac output (measured in L/min) is the volume of blood expelled by the heart per beat (stroke volume) multiplied by the heart rate. An abnormal cardiac output is at least one indicator of cardiovascular disease.

The current standard method for measuring cardiac output is the thermodilution technique (Darovic, G. O. Hemodynamic monitoring: invasive and noninvasive clinical application. 2nd Ed. W.B. Saunders, 1995). Generally, the technique involves injecting a thermal indicator (cold or heat) into the right side of the heart and detecting a change in temperature caused as the indicator flows into the pulmonary artery.

Typically, the thermodilution technique involves inserting a flow-directed balloon catheter (such as a Swan-Ganz catheter) into a central vein (basilic, internal jugular or subclavian) and guiding it through the right atrium and ventricle to the pulmonary artery. The balloon catheter is typically equipped with a thermistor near its tip for detecting changes in blood temperature. A rapid injection of a bolus of chilled glucose solution (through a port in the catheter located in the vena cava near the right atrium) results in a temperature change in the pulmonary artery detected with the thermistor. The measured temperature change is analyzed with an external electronic device to compute the cardiac output. The algorithm implemented in this computation is typically a variant of the Stewart-Hamilton technique and is based on the theory of indicator mixing in stirred flowing media (Geddes L A, Cardiovascular devices and measurements. John Wiley & Sons. 1984).

Thermodilution measurements of cardiac output are disadvantageous for several reasons. First, placement of the thermodilution balloon catheter is an expensive and invasive technique requiring a sterile surgical field. Second, the catheter left in place has severe risks to the patient such as local infections, septicemia, bleeding, embolization, catheter-induced damage of the carotid, subclavian and pulmonary arteries, catheter retention, pneumothorax, dysrrhythmias including ventricular fibrillation, perforation of the atrium or ventricle, tamponade, damage to the tricuspid values, knotting of the catheter, catheter transection and endocarditis. Third, only specially trained physicians can insert the balloon catheter for thermodilution cardiac output. Last, thermodilution measurements of the cardiac output are too invasive to be performed in small children and infants.

Another method used for measuring cardiac output is the dye indicator dilution technique. In this technique, a known volume and concentration of indicator is injected into the circulatory flow. At a downstream point, a blood sample is removed and the concentration of the indicator determined. The indicator concentration typically peaks rapidly due to first pass mixing of the indicator and then decreases rapidly as mixing proceeds in the total blood volume (~10 seconds; first pass concentration curve). Further, indicator concentration slowly diminishes as the indicator is metabolized and removed from the circulatory system by the liver and/or kidneys (time depending upon the indicator used). Thus, a concentration curve can be developed reflecting the concentration of the indicator over time. The theory of indicator dilution predicts that the area under the first pass concentration curve is inversely proportional to the cardiac output.

Historically, indicator dilution techniques have involved injecting a bolus of inert dye (such as indocyanine green) into a vein and removing blood samples to detect the concentration of dye in the blood over time. For example, blood samples are withdrawn from a peripheral artery at a constant rate with a pump. The blood samples are passed into an optical sensing cell in which the concentration of dye in the blood is measured. The measurement of dye concentration is based on changes in optical absorbance of the blood sample at several wavelengths.

Dye-dilution measurements of cardiac output have been found to be disadvantageous for several reasons. First, arterial blood withdrawal is time consuming, labor intensive and depletes the patient of valuable blood. Second, the instruments used to measure dye concentrations (densitometer) must be calibrated with samples of the patient's own blood containing known concentrations of the dye. This calibration process can be very laborious and time consuming in the context of the laboratory where several samples must be run on a daily basis. Further, technical difficulties arise in extracting the dye concentration from the optical absorbance measurements of the blood samples.

A variation on the dye-dilution technique is implemented in the Nihon Kohden pulse dye densitometer. In this technique, blood absorbance changes are detected through the skin with an optical probe using a variation of pulse oximetry principles. This variation improves on the prior technique by eliminating the necessity for repeated blood withdrawal. However, as described above, this technique remains limited by the difficulty of separating absorbance changes due to the dye concentration changes from absorbance changes due to changes in blood oxygen saturation or blood content in the volume of tissue interrogated by the optical probe. This method is also expensive in requiring large amounts of dye to create noticeable changes in absorbance and a light source producing two different wavelengths of light for measuring light absorption by the dye and hemoglobin differentially. Even so, the high background levels of absorption in the circulatory system make this technique inaccurate. Finally, where repeat measurements are desired, long intervals must ensue for the high levels of the indicator to clear from the blood stream. Thus, this technique is inconvenient for patients undergoing testing and practitioners awaiting results to begin or alter treatment.

Other approaches for measuring cardiac output exist which are not based on indicator dilution principles. These include ultrasound Doppler, ultrasound imaging, the Fick principle applied to oxygen consumption or carbon dioxide production and electric impedance plethysmography (Darovic, supra). However, these techniques have specific limitations. For instance, the ultrasound techniques (Doppler and imaging) require assumptions on the three-dimensional shape of the imaged structures to produce cardiac output values from velocity or dimension measurements.

Blood volume measures the amount of blood present in the cardiovascular system. Blood volume is also a diagnostic measure that is relevant to assessing the health of a patient. In many situations, such as during or after surgery, traumatic accident or in disease states, it is desirable to restore a patient's blood volume to normal as quickly as possible. Blood volume has typically been measured indirectly by evaluating multiple parameters (such as blood pressure, hematocrit, etc.). However, these measures are not as accurate or reliable as direct methods of measuring blood volume.

Blood volume has been directly measured using indicator dilution techniques (Geddes, supra). Briefly, a known amount of an indicator is injected into the circulatory system. After injection, a period of time is allowed to pass such that the indicator is distributed throughout the blood, but without clearance of the indicator from the body. After the equilibration period, a blood sample is drawn which contains the indicator diluted within the blood. The blood volume can then be calculated by dividing the amount of indicator injected by the concentration of indicator in the blood sample (for a more detailed description see U.S. Pat. No. 6,299,583 incorporated by reference). However, to date, the dilution techniques for determining blood volume are disadvantageous because they are limited to infrequent measurement due to the use of indicators that clear slowly from the blood.

In the dye dilution method, the dye must be injected as a rapid intravenous bolus, not as a continuous infusion, as the latter does not result in the characteristic dye dilution curve needed for the calculation of cardiac output. Choice of the injection method and volume of the injectate are relevant to the measured cardiac output and the variability of sequential measurements of cardiac output obtained with transcutaneous fluorescence dye dilution. The venous system targeted by the injection is characterized by branching veins and venous valves. These present an inherent resistances to injection which contributes to a potential fragmentation of the bolus, as well as to a pooling and delayed release of any residual dye. These can be noted, respectively, by fluctuations in the morphology of the dye dilution curve and a prolongation of the tail of the dye bolus.

Furthermore, cardiovascular disease is highly prevalent in patients with end-stage renal disease. Patients whose kidney function is insufficient to eliminate metabolic byproducts and water undergo kidney dialysis several times every week to clear their blood from these products. Typically, large needles are inserted at the level of an arterio-venous (AV) fistula or a synthetic AV graft in the arm of the patient and connected to the dialyzer for several hours during the procedure.

Fluid accumulation between dialysis sessions is mostly in the extravascular space. Fluid removal during dialysis is from the vascular space. If the rate of fluid transfer from the extravascular space to the vascular space does not match the rate of fluid removal, the patient experiences hypovolemia, which reduces cardiac output, blood pressure and peripheral perfusion. Hypotension resulting from a rapid decrease of the circulating blood volume is the most common complication from the dialysis procedure.

Current methods of monitoring fluid status in dialysis patients rely on weighing the patient before and after the dialysis procedure to assess the total fluid volume removed and on measuring changes in hematocrit during the procedure. Since the amount of red blood cells in the circulating blood does not change, the hematocrit increase during the dialysis can be used to track the blood volume change resulting from the procedure. Patient weighing does not provide intradialysis monitoring. Tracking relative changes of the blood volume based on hematocrit measurement is affected by the initial blood volume at the patient at the beginning of the dialysis session, which varies from session to session. Furthermore, it has been suggested that central blood volume, the volume of blood in the large vessels (primarily large veins) is more important than total blood volume with respect to maintaining cardiac filling, blood pressure and peripheral perfusion.

SUMMARY

The present cardiovascular measurement devices and methods assess cardiovascular parameters within the circulatory system using indicator dilution techniques. In particular, the present cardiovascular measurement devices and methods assess cardiac output and circulating blood volume of patients undergoing kidney hemodialysis from a measurement on the body surface or at the connection of the dialyzer with the patient of the fluorescence dilution recording observed following injection of an inert fluorescent dye in the venous bloodstream.

In one aspect of the present cardiovascular measurement devices and methods, a non-invasive method for determining cardiovascular parameters is described. In particular, a non-invasive fluorescent dye indicator dilution method is used to evaluate cardiovascular parameters. The method may be minimally invasive, requiring only a single peripheral, intravenous line for indicator injection into the circulatory system of the patient. Further, a blood draw may not be required for calibration of the system. Further, cardiovascular parameters may be evaluated by measuring physiological parameters relevant to assessing the function of the heart and circulatory system. Such parameters include, but are not limited to cardiac output and blood volume.

Such minimally invasive procedures are advantageous over other methods of evaluating the cardiovascular system. First, complications and patient discomfort caused by the procedures are reduced. Second, such practical and minimally invasive procedures are within the technical ability of most doctors and nursing staff, thus, specialized training is not required. Third, these minimally invasive methods may be performed at a patient's bedside or on an outpatient basis. Finally, methods may be used on a broader patient population, including patients whose low risk factors may not justify the use of central arterial measurements of cardiovascular parameters.

In another aspect of the cardiovascular measurement devices and methods, these methods may be utilized to evaluate the cardiovascular parameters of a patient at a given moment in time, or repeatedly over a selected period of time. The dosages of indicators and other aspects of the method can be selected such that rapid, serial measurements of cardiovascular parameters may be made. These methods can be well suited to monitoring patients having cardiac insufficiency or being exposed to pharmacological intervention over time. Further, the non-invasive methods may be used to evaluate a patient's cardiovascular parameters in a basal state and when the patient is exposed to conditions which may alter some cardiovascular parameters. Such conditions may include, but are not limited to changes in physical or emotional conditions, exposure to biologically active agents or surgery. For example, embodiments of the cardiovascular measurement devices and methods can be used for cardiac output monitoring before, during, or after kidney dialysis; cardiac output monitoring under shock conditions (such as, for example, septic shock, anaphylactic shock, cardiogenic shock, neurogenic shock, hypovolemic shock); cardiac output monitoring during stress tests to better understand the heart's ability to increase blood supply to the heart and body while exercising or under other conditions requiring additional blood flow through the heart; cardiac output monitoring before, during, and after chemotherapy treatment to monitor fluid equilibrium in the body; and cardiac output measurements for athletes needing to understand how their cardiac performance to improve their athletic performance.

In another aspect of the cardiovascular measurement devices and methods, modifications of the method may be undertaken to improve the measurement of cardiovascular parameters. Such modifications may include altering the placement of a photodetector relative to the patient or increasing blood flow to the detection area of the patient's body.

In yet another aspect of the cardiovascular measurement devices and methods, the non-invasive method of assessing cardiovascular parameters utilizes detection of indicator emission, which is fluorescence, as opposed to indicator absorption. Further, indicator emission may be detected in a transmission mode and/or reflection mode such that a broader range of patient tissues may serve as detection sites for evaluating cardiovascular parameters, as compared to other methods. Measurement of indicator emission can be more accurate than measurements obtained by other methods, as indicator emission can be detected directly and independent of the absorption properties of whole blood.

In a further aspect of the cardiovascular measurement devices and methods, a system for the non-invasive or minimally invasive assessment of cardiovascular parameters is described. In particular, such a system may include an illumination source for exciting the indicator, a photodetector for sensing emission of electromagnetic radiation from the indicator and a computing system for receiving emission data, tracking data over time and calculating cardiovascular parameters using the data.

In another aspect of the cardiovascular measurement devices and methods, the methods and system described herein may be used to assess cardiovascular parameters of a variety of subjects. In some embodiments, the methodology can be modified to examine animals or animal models of cardiovascular disease, such as cardiomyopathies. The cardiovascular measurement devices and methods are advantageous for studying animals, such as transgenic rodents whose small size prohibits the use of current methods using invasive procedures. The present cardiovascular measurement devices and methods are also advantageous in not requiring anesthesia which can effect cardiac output measurements.

In yet another aspect of the cardiovascular measurement devices and methods, a noninvasive calibration system can be used to determine the concentration of circulating indicator dye. In some embodiments, the concentration of circulating indicator dye can be determined from the ratio of emergent fluorescent light to transmitted and/or reflected excitation light.

In yet another aspect of the cardiovascular measurement devices and methods, a method for injection of the dye can improve the accuracy of the cardiac measurements. In some embodiments, the injection method comprises intravenous rapid bolus injection of a minimum volume of fluorescent dye followed by a rapid bolus injection of an inert solution (vehicle) without the dye.

In yet another aspect of the cardiovascular measurement devices and methods, a method for measuring cardiac output parameters comprises determining non-invasively and transcutaneously the cardiac output and circulating blood volume of patients undergoing kidney hemodialysis from a measurement on the body surface or at the connection of the dialyzer with the patient of the fluorescence dilution recording observed following injection of an inert fluorescent dye in the venous bloodstream. The measurement site may be illuminated with a light source that causes the dye circulating with the bloodstream to fluoresce and the fluorescence signal can be recorded transcutaneously or across the connection tubes between the patient and the dialyzer.

In yet another aspect of cardiovascular measurement devices and methods, a method of calibration of a probe for a kidney dialysis system has been disclosed since, as fluid is removed from the vascular space, the circulating blood hematocrit increases and the blood becomes more concentrated in hemoglobin. The increase of the blood hematocrit changes the optical properties of the blood. To quantify these effects and find a way to calibrate the fluorescence signal, a model of the propagation of light in a blood slab containing ICG has been made allowing the ICG concentration and the hemoglobin content of the blood to vary. The model was used to develop a method of calibration that determines the concentration of the fluorescent indicator ICG as a function of the fluorescence signal independently of variations of the hemoglobin content of the blood.

In other embodiments of the cardiovascular measurement devices and methods, the methodology can be modified for clinical application to human patients. The present cardiovascular measurement devices and methods may be used on all human subjects, including adults, juveniles, children and neonates.

BRIEF DESCRIPTION OF THE DRAWINGS

FIGS. 22A-C is a depiction of multiple views of an alternative embodiment of a probe used in a hemodialysis process.

DETAILED DESCRIPTION

The method and system of the present cardiovascular measurement devices and methods are for the evaluation of cardiovascular parameters of a subject using an indicator dilution technique.

Figure 9:
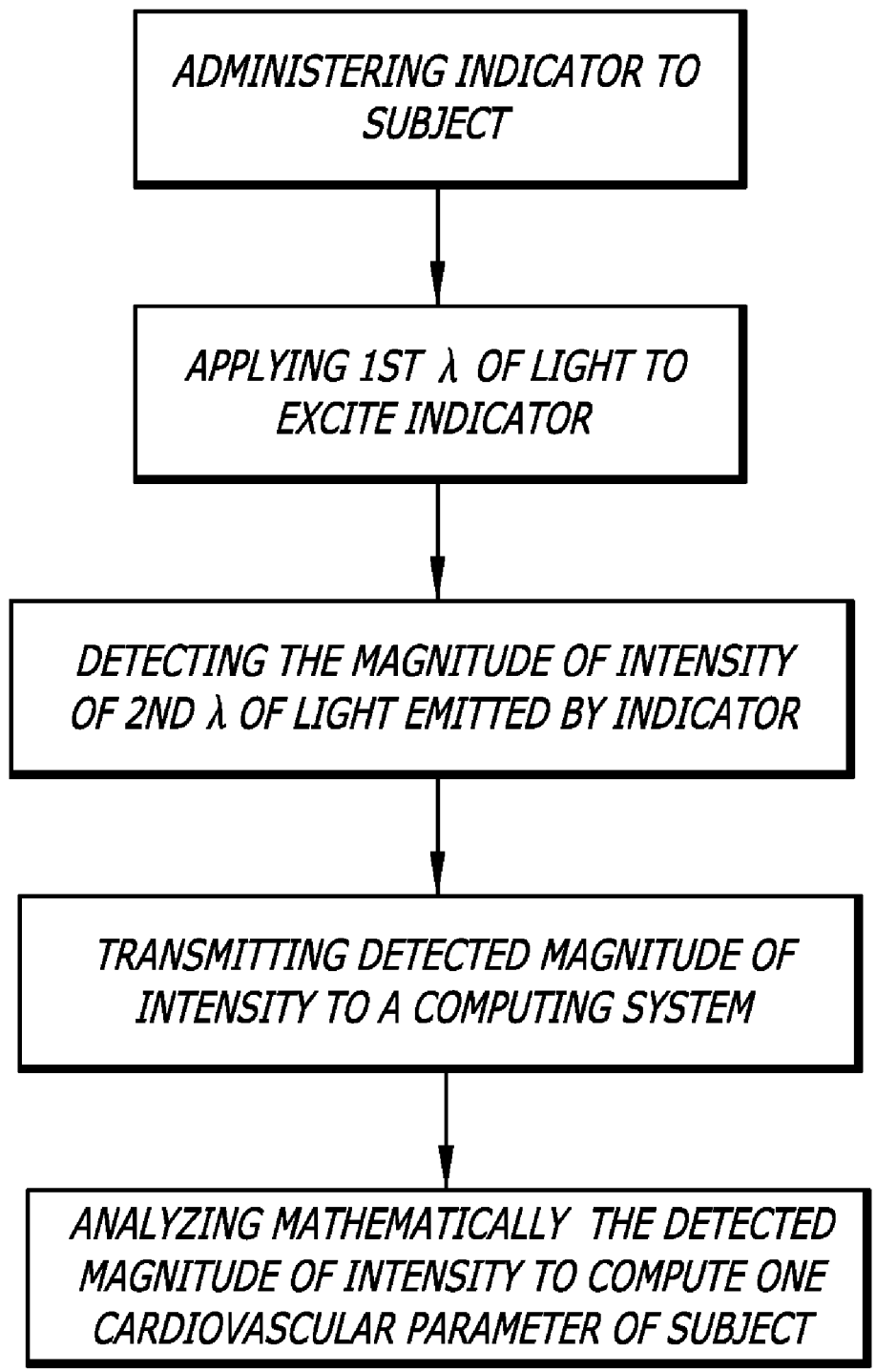
FIG. 9 is a flow chart depicting one exemplary cardiac output measurement.

The method of cardiac output generally involves the injection of a selected amount of indicator into the bloodstream of the subject (FIG. 9). The indicator can be illuminated using a first wavelength of excitation light selected to cause the indicator to fluoresce and emit a second wavelength of light. A photodetector can be placed near the subject for the detection of the intensity of the emitted second wavelength of light, which is proportional to the concentration of the indicator circulating within the circulatory system. The photodetector transmits this intensity information to a computing system, which records and preferably maps the intensity curve of the indicator detected over time.

Typically, the indicator concentration values increase to a peak rapidly after injection of the indicator. Then, the concentration values decrease rapidly, then more steadily as the indicator is mixed throughout the body circulatory system and metabolized over time. A microprocessor driven computation then can calculate from the concentration curve, the patient's cardiac output and/or blood volume values. Additionally, values can be generalized repeatedly using this method, at intervals of about every 2-5 minutes.

Indicators.

The indicators useful in the cardiovascular measurement devices and methods may be inert and biocompatible in that they should not alter cardiovascular parameters such as heart rate. Further, the indicator may be a substance that once injected, does not diffuse out of the vasculature of the cardiovascular system. Also, the indicator may be selected to be one which is metabolized within the body at a rate such that repeated measures using this method may be conducted at intervals of about 2-5 minutes. It is also desirable that the background levels of circulating indicator be cleared between intervals, although measurements may be taken when background levels are not zero. Finally, the indicator can be selected to be detectable by the photodetector system selected.

In an exemplary embodiment, a non-invasive dye indicator dilution method may be used to evaluate cardiovascular function. Many different dye indicators may be used. The dye indicator may be fluorescent, having an excitation wavelength and an emission wavelength in the near infrared spectrum, preferably about 750 nm to about 1000 nm, and more preferably about 750 nm to about 850 nm.

For example, the indicator used may be indocyanine green (ICG; purchased for example from Akorn, Decatur or Sigma, St. Louis, Mo.; commercial names: Diagnogreen©, ICGreen©, Infracyanine©, Pulsion©). ICG has been previously been used to study the microcirculation of the eye, the digestive system and liver function (Desmettre, T., J. M. Devoisselle, and S. Mordon. Fluorescence properties and metabolic features of indocyanine green (ICG) as related to angiography. Sury Ophthalmol 45, 15-27, 2000). ICG fluoresces intensely when excited at near infrared wavelengths. ICG in blood plasma has a peak fluorescence of about 810 to 830 nm with an optimal excitation wavelength of about 780 nm (Hollins, supra; Dorshow, supra). ICG breaks down quickly in aqueous solution, and metabolites are not fluorescent, minimizing recirculation artifact and reducing the time period between which measurements can be made. The wavelength of emission of ICG is also within the optical window (750-1000 nm) in which living tissues are relatively transparent to light.

Other biocompatible fluorescent dyes such as fluorescein and rhodamine would also be suitable in the cardiovascular measurement devices and methods. Fluorescein in blood plasma has a peak fluorescence of about 518±10 nm with an optimal excitation wavelength of about 488 nm (Hollins, supra; Dorshow, supra). Rhodamine in blood plasma has a peak fluorescence of about 640±10 nm with an optimal excitation wavelength of about 510 nm.

Indicator Injection and Dosage.

The dosage of indicator can be selected such that an amount used is non-toxic to the subject, is present in the circulatory system for an amount of time adequate to establish an indicator concentration curve, but is metabolized in an amount of time such that repeated measurements can be conducted at intervals of about 2-5 minutes apart. Further, the indicator can be administered to the subject by injection into a vein.

In one exemplary embodiment, a dosage of about 0.015 mg/kg may be used as this dose leads to peak blood concentrations below 0.002 mg/ml. In this concentration range, the measurement of the circulating indicator concentration is linearly related to the intensity of the emission wavelength detected. For example, in a laboratory animal model, about 0.045 mg can be injected into a 3 kg rabbit (blood volume=200 ml) such that the average circulating concentration is about 0.00023 mg/ml whole blood.

Dye dilution techniques have been applied in humans in other methods and systems using indocyanine green as a dye. Living tissues of humans and animals are relatively transparent for near infrared wavelengths of light which allows for transmission of light across several mm of tissue and transcutaneous detection of the fluorescence emission of ICG. The use of dosages in the ranges stated above is additionally suitable for human use.

In an exemplary embodiment, the injection method comprises intravenous rapid bolus injection of a minimum volume of fluorescent dye followed by a rapid bolus injection of an inert solution or vehicle (such as saline, for example) without the dye. For example, for an average 70 kg male, the injection method could include a 1.5 ml injection of the dye in solution, followed by a 3-5 ml flush with the vehicle (physiologic inert solution), each delivered over 1-2 seconds. The volumes and rates of injection would be expected to be different between application of this method in infants, children and adults, with the doses for infants and children being scaled down when compared to the adult doses. In some embodiments, the dye and the vehicle without the dye could be delivered in separate syringes, through a combination of a syringe and a fluid filled bag, or through a double barrel syringe or single syringe with separate compartments. The injection could either be delivered manually or using an automatic injector. If an automatic injector were employed, injection could be triggered by an external signal such as the subject's respiratory cycle, electrocardiogram or other biologic signal.

In most clinical or biological applications demanding bolus intravenous injection, the speed of injection, the volume of the bolus and whether or not the bolus is followed by a flush is typically not critical. In the thermodilution method, rapid injection may be helpful to obtain optimal signals for the thermodilution curve necessary for the calculation of cardiac output. In the thermodilution method, however, contrary to the dye dilution method, the volume of the injectate may not be too small. A bolus of small volume would result in excessive thermal losses of the injectate prior to reaching the sensing thermistor at the catheter's tip, with a resultant loss of the detected thermodilution signal. Typical volumes of injection for adults undergoing cardiac output measurement with the thermodilution method are 10 ml of an iced solution, with volumes substantially less resulting in questionable results. This compares to 1.5 ml typically used as the volume of injection for the transcutaneous dye dilution method of measuring cardiac output. Substantially larger volumes may present problems because of the prolonged duration to make such injections into a peripheral vessel and consequent susceptibility of the bolus to pooling and fragmentation. While the injectate in the thermodilution method is typically delivered with an invasive balloon catheter by an injection port deep in the venous compartment near the right atrium, the injectate in the fluorescence dye dilution method may be delivered through a short (1-2 in) catheter inserted in a peripheral vein.

Illumination Source.

The illumination sources useful in cardiovascular measurement devices and methods may be selected to produce an excitation wavelength in the near infrared spectrum, in some embodiments about 750 nm to about 1000 nm, and in other exemplary embodiments about 750 to about 850 nm. This selection is advantageous in at least that most tissues are relatively transparent to wavelengths in this range. Thus, in some embodiments, an indicator in the blood stream is excitable transcutaneously and indicator emission can be detected transcutaneously. Further, blood constituents do not fluoresce at these wavelengths, thus there may be no other contributor to the measured fluorescence emission signal. Therefore, this method is advantageous in that at least the sensitivity of detection in this method is improved over other methods, which measure indicator absorption, as opposed to emission.

However, it is within the scope of the cardiovascular measurement devices and methods to use other wavelengths of light, for example in the visible range of the spectrum as some tissues are relatively transparent even at these wavelengths. Selection of the illumination source, therefore, can depend in part on the indicator selected and the tissue from which detection will be made. The illumination source may be selected to result in the peak emission wavelength of the indicator.

Examples of illumination sources which may be used in the cardiovascular measurement devices and methods include, but are not limited to lamps, light emitting diodes (LEDs), lasers or diode lasers.

In some embodiments, modifications to the system or illumination source may be altered to further to maximize the sensitivity or accuracy of the system for measuring indicator concentration. For example, in some embodiments, the excitation wavelength produced by the illumination source will be steady. Alternatively, the excitation wavelength produced by the illumination source can be modulated to allow for a lock-in detection technique. The excitation light can also be chopped to allow for a boxcar integration detection technique.

For example, the illumination source may emit light in a periodic varying pattern having a fixed frequency and the emission recorded by the photodetector read at the same frequency to improve the accuracy of the readings. The periodic varying pattern and frequency can be selected to improve noise-rejection and should be selected to be compatible with the rest of the instrumentation (such as the light source and photodetector).

The illumination source may be adapted to target a detection area of the subject's tissue from which emission wavelength intensity will be recorded. In some embodiments, the illumination source may comprise an optic fiber for directing the excitation light to the detection area. In some embodiments, the illumination source may comprise mirrors, filters and/or lenses for directing the excitation light to the detection area.

Detection Areas.

The target detection area is that location of a subject's tissue which is exposed to the excitation wavelength of light and/or from which the emission wavelength light intensity output may be measured.

The method of detection may be non-invasive. In these embodiments, a detection area can be selected such that a photodetector can be placed in proximity to the detection area and emission wavelength light intensity measured. The photodetector may be placed transdermally to at least one blood vessel, and in some embodiments transdermally to a highly vascularized tissue area. Examples of detection areas include, but are not limited to fingers, auricles of the ears, nostrils and areas having non-keratinized epithelium (such as the nasal mucosa or inner cheek). In alternative embodiments, the method of detection is minimally invasive. For example, the photodetector can be placed subdermally (within or beneath the epidermis) and proximate to at least one blood vessel or in a perivascular position.

In yet alternative exemplary embodiments, the method of detection is minimally invasive. For example, the photodetector can be placed intravascularly to detect indicator emissions, such as within an artery. In such embodiments, an external probe for emitting and receiving light may not be needed. For example, in some embodiments the probe may include a fiber optic located within an intravascular catheter. Specifically, the device may include an intravascular catheter made of biocompatible plastic material which contains, embedded in the catheter wall, an optical fiber that ends at or near the tip of the catheter. For example, the catheter may have a diameter of 100 µm or less. The fiber optic can be used to optically sense the presence and concentration of endogenous substances in the blood or exogenous substances injected or infused in the blood stream through the catheter lumen or another catheter. A fiber optic connector at the proximal external end of the fiber optic connects the fiber to an external monitor. In use, the needle of an injection syringe can be inserted through the catheter lumen and used to inject the indicator material (meanwhile the catheter may be allowed to remain within the vein or artery). The injection needle may be withdrawn from the catheter after injection. After the indicator has been injected and the indicator has had sufficient time to circulate through the cardiovascular system, light from a light source can be directed to the blood and circulated indicator via the optical fiber embedded in the catheter. The optical fiber of the catheter may also be used to receive light from the indicator and transmit the light to the monitor. In alternative embodiments, the catheter may include a plurality of optical fibers for transmitting and/or receiving light used to obtain measure parameters of interest of the cardiovascular system. Catheters that include optical fibers are described in U.S. Pat. Nos. 4,730,622 to Cohen and 5,217,456 to Narciso, the entire contents of each of which are incorporated by reference. In addition, other sensing devices and mechanisms may be included in the intravascular probe.

Additionally, the detection area may be arterialized during indicator emission detection. Examples of conditions resulting in detection area arterialization include, but are not limited to heating or exposure to biologically active agents which effect sympathetic system blockade (such as lidocaine).

Photodetector.

The detection of indicator emissions can be achieved by optical methods known in the art. Measurement of indicator concentration can be made by administering a detectable amount of a dye indicator and using either a non-invasive, minimally invasive or intravascular procedures preferably for continuous detection. The photodetector may be positioned proximately to the detection area of the subject. The photodetector may be positioned distally or proximately to the site of the illumination source.

Fluorescent light is emitted from the indicator with the same intensity for all directions (isotropy). Consequently, in some embodiments, the emission of the dye can be detected both in "transmission mode" when the excitation light and the photodetector are on opposite sides of the illuminated tissue and in "reflection mode" when the excitation and the photodetector are on the same side of the tissue. This is advantageous over other methods at least in that the excitation light and emitted light can be input and detected from any site on the body surface and not only optically thin structures.

Photodetectors may be selected to detect the quantities and light wavelengths (electromagnetic radiation) emitted from the selected indicator. Photodetectors having sensitivity to various ranges of wavelengths of light are well known in the art.

In some embodiments, modifications to the system are made to further enhance the sensitivity or accuracy of the system for measuring indicator concentration. For example in some embodiments, the detection system can incorporate a lock-in detection technique. For example, the excitation light may be modulated at a specific frequency and a lock-in amplifier can be used to amplify the output of the photodetector only at that frequency. This feature is advantageous in at least that it further improves the sensitivity of the system by reducing signal to noise and allows detection of very small amounts of fluorescence emission.

In some embodiments a photomultiplier tube can be utilized as or operably connected with another photodetector to enhance the sensitivity of the system. Finally, in some embodiments, additional features, such as filters, may be utilized to minimize the background of the emission signals detected. For example, a filter may be selected which corresponds to the peak wavelength range or around the peak wavelength range of the indicator emission.

The detected electromagnetic radiation can be converted into electrical signals by a photoelectric transducing device which is integral to or independent of the photodetector. These electrical signals are transmitted to a microprocessor which records the intensity of the indicator emissions as correlated to the electrical signal for any one time point or over time. (For an example of such a device see U.S. Pat. No. 5,766,125, herein incorporated by reference.)

System Calibration

A) Minimally Invasive Calibration

The method may be minimally invasive in requiring only a single peripheral blood draw from the circulatory system to be taken for calibration purposes. Indicator concentration may be measured continuously and non-invasively using a photodetector. One blood sample from the subject may be withdrawn for calibration of the actual levels of circulating indicator with the indicator levels detected by the system. For example, a blood sample may be drawn from the subject at a selected time after the administration of the indicator into the blood stream. The blood sample may then be evaluated for the concentration of indicator present by comparison with a calibration panel of samples having known indicator concentrations. Evaluation of the indicator concentration may be made spectrophotometrically or by any other means known in the art. Where the subject blood concentration of indicator falls within a range of about 0.001 to about 0.002 mg/ml, the concentration-fluorescence curve is linear and it crosses the origin of the axes, that is the fluorescence is zero when the concentration is zero. Therefore a single measurement point suffices to define the calibration curve, and no further blood samples need be taken.

B) Noninvasive Calibration

In another embodiment no blood draw is required for calibration of this system. It is noted that the fluorescence of some indicators, such as ICG, does not substantially vary from patient to patient and that the skin characteristics are relatively constant for large classes of patients. Thus, the fluorescence in the blood of the patient measured from a given site on the body surface can be converted in an absolute measurement of ICG concentration, once the curve of indicator concentration vs. fluorescence is defined for that site of measurement.

In an exemplary embodiment using noninvasive calibration, the concentration of a fluorescent indicator (ICG) injected in the bloodstream can be determined without taking a blood sample. A probe (including or connected to one or several photodetectors, as described above) can measure the intensity of fluorescent light emitted by the ICG indicator when illuminated by a light source in or near the skin. The probe can also measure the intensity of the light from that source that is reflected by or transmitted through the illumination skin site. Since the ratio of emergent fluorescent light to transmitted excitation light is directly proportional to ICG concentration (see FIGS. 11A-D, FIGS. 12A-12D, and Example 3 below), the concentration of ICG can be determined from the ratio of emergent fluorescent light to transmitted excitation light. For example, the graph in FIG. 11C shows that ICG concentration is directly proportional to the ratio of fluorescent light to transmitted excitation light. In another example illustrated by the graph of FIG. 12C, ICG remains directly proportional to the ratio of fluorescent light to transmitted excitation light even when factoring the variations of absorption properties for hemoglobin (Hb) and ICG with wavelength and the absorption by bloodless tissue. While the slopes of the lines in FIG. 12C vary slightly depending upon hemoglobin content, the differences between the light ratios are relatively small. The ratios may be normalized by creating a table of coefficients that take into account various factors that may affect the light ratios (such as absorption by bloodless tissue, hemoglobin content, path length, skin color, moisture on skin surfaces, body hair, and other factors known to those skilled in the art).

The probe used to transmit and receive light may include a single optical fiber, multiple optical fibers for transmitting and/or receiving light, or other configuration known to those skilled in the art. The excitation light that is received and used in the ratio against fluorescence may be reflected and/or transmitted light. For example, in one embodiment, the light transmitter and receiver can be on the same skin surface so that the receiver can receive light reflected from the tissue. In such an embodiment, the receiving and transmitting element are the same optical fiber (See Diamond et al., "Quantification of fluorophore concentration in tissue-simulating media by fluorescence measurements with a single optical fiber;" *Applied Optics*, Vol. 42, No. 13, May 2003; the contents of which are incorporated herein by reference). In other embodiments, they may be different optical fibers (or other devices known to those skilled in the art). In such embodiments, the various optical fibers may be spatially positioned in relation to each other to optimize measurement, as described in Weersink et al. (See Weersink et al., "Noninvasive measurement of fluorophore concentration in turbid media with a simple fluorescence/reflectance ratio technique;" *Applied Optics*, Vol. 40, No. 34, December 2001; and U.S. Pat. No. 6,219,566 to Weersink et al.; the contents of both of which are incorporated herein by reference). In another embodiment, the transmitter and receiver are positioned substantially opposite each other to allow transmission of the light (such as forward scattering) from the transmitter, through the tissue, and out of the tissue to the receiver on the other side of the tissue.

C) Noninvasive Hemodialysis Probe Calibration

In another exemplary embodiment of a non-invasive calibration process of a hemodialysis process the concentration of a fluorescent indicator (ICG) injected in the bloodstream can be determined without taking a blood sample. During kidney dialysis, as fluid is removed from the vascular space, the circulating blood hematocrit increases and the blood becomes more concentrated in hemoglobin. The increase of the blood hematocrit changes the optical properties of the blood. The light absorption and light scattering increase as the density of red blood cells and the hemoglobin content of the blood increase. As the optical properties of the blood change, the relationship between the fluorescence of ICG in blood and the ICG concentration changes. This effect complicates the calibration of the fluorescence signal as a function of circulating ICG concentration in the dialyzer tubing.

Figure 13:
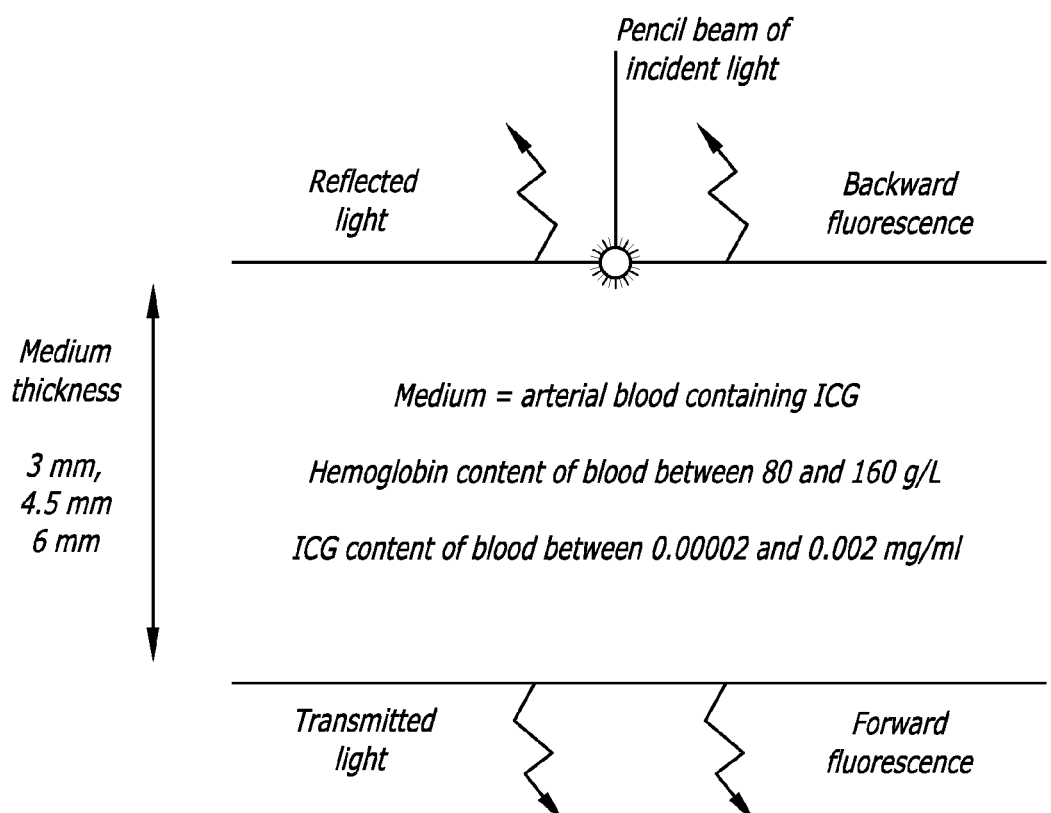
FIG. 13 is a depiction of a model used in calibration of the hemodialysis system.

To quantify these effects and find a way to calibrate the fluorescence signal, we have modeled a propagation of light in a blood slab containing ICG allowing the ICG concentration and the hemoglobin content of the blood to vary (See FIG. 13). The model study pointed to a calibration equation to derive the concentration of ICG from the fluorescence remitted from the blood medium and the transmitted light intensity across the blood medium or the light intensity reflected by the blood medium.

Model Study

The model as shown in FIG. 13 has used the Monte-Carlo method to simulate the transport of light from a pencil beam that shines on a semi-infinite slab of blood. The medium thickness is set to be 3, 4.5, or 6 mm (the dialyzer tube has a diameter of 4.5 mm). The optical properties of the blood in the slab are adjusted to match those of blood with a hemoglobin content comprised between 80 and 160 g/L, an excitation wavelength of 784 nm, and an ICG fluorescence emission wavelength of 830 nm. The blood is assumed to be fully saturated in $O_2$ (since arterial blood is pumped into the dialyzer). The blood contains ICG with a concentration between $2.10^{-5}$ μg/μL and $2.10^{-3}$ μg/μL. (the peak ICG concentration in human blood in our clinical trial is approximately $2.10^{-3}$ μg/μL when the injected ICG dose is 1 mg). The Monte Carlo program was developed following the approach of Wang et al. (Wang, L. Jacques, S L. Zheng, L. MCML—Monte Carlo modeling of light transport in multi-layered tissues. Computer Methods & Programs in Biomedicine. 47(2):131-46, 1995).

The simulation follows 1,500,000 photons as they propagate in the medium and occasionally transform into fluorescent photons. Emerging photons at the wavelength of the incident light are tabulated as a function of the distance between the point of incidence and the point of emergence on the side of the illumination beam (reflected light) and on the opposite side to the illumination beam (transmitted light). Likewise, fluorescent photons are tabulated as a function of the distance between the point of incidence and the point of emergence on the side of the illumination beam (back fluorescence) and on the opposite side (forward fluorescence). While the simulation keeps track of the angle between the direction of the emergent photons and the normal to the surface of the medium, all photons are added in the results presented in this summary which is akin to using detectors with large angles of acceptance.

We present here the results for the 4.5 mm thick blood slab. Results for the other thicknesses reflect similar behaviors. (The reflectance and back-fluorescence signals are essentially the same for the three thicknesses. The transmittance decreases as the thickness increases but the transmittance intensity can still be used to correct for changes of the back-fluorescence with hemoglobin content.)

Figure 14A:
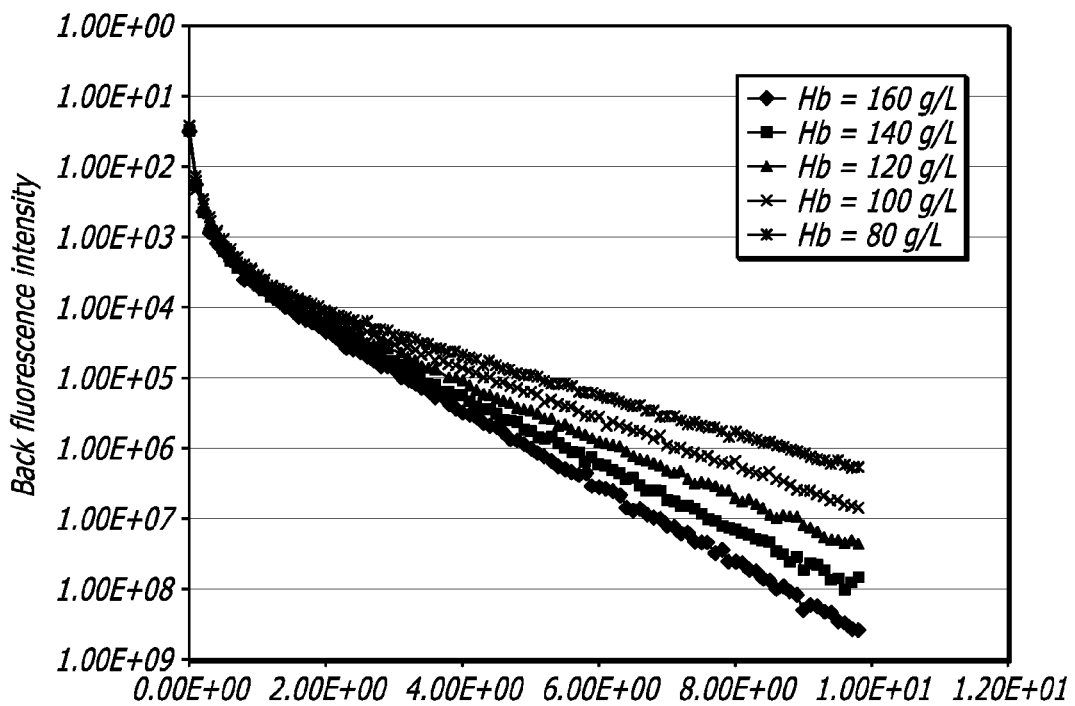
FIGS. 14A-C illustrate light intensity profiles for back-fluorescence, transmittance and reflectance for a blood ICG concentration, respectively.
Figure 14B:
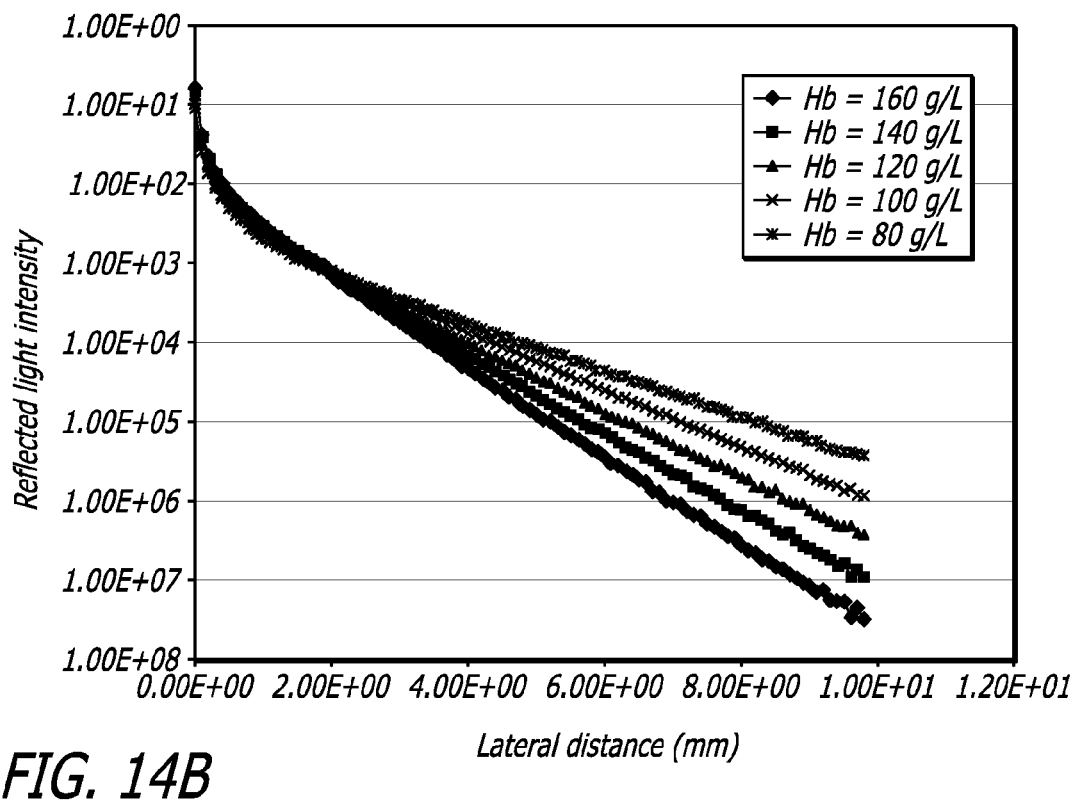
Figure 14C:
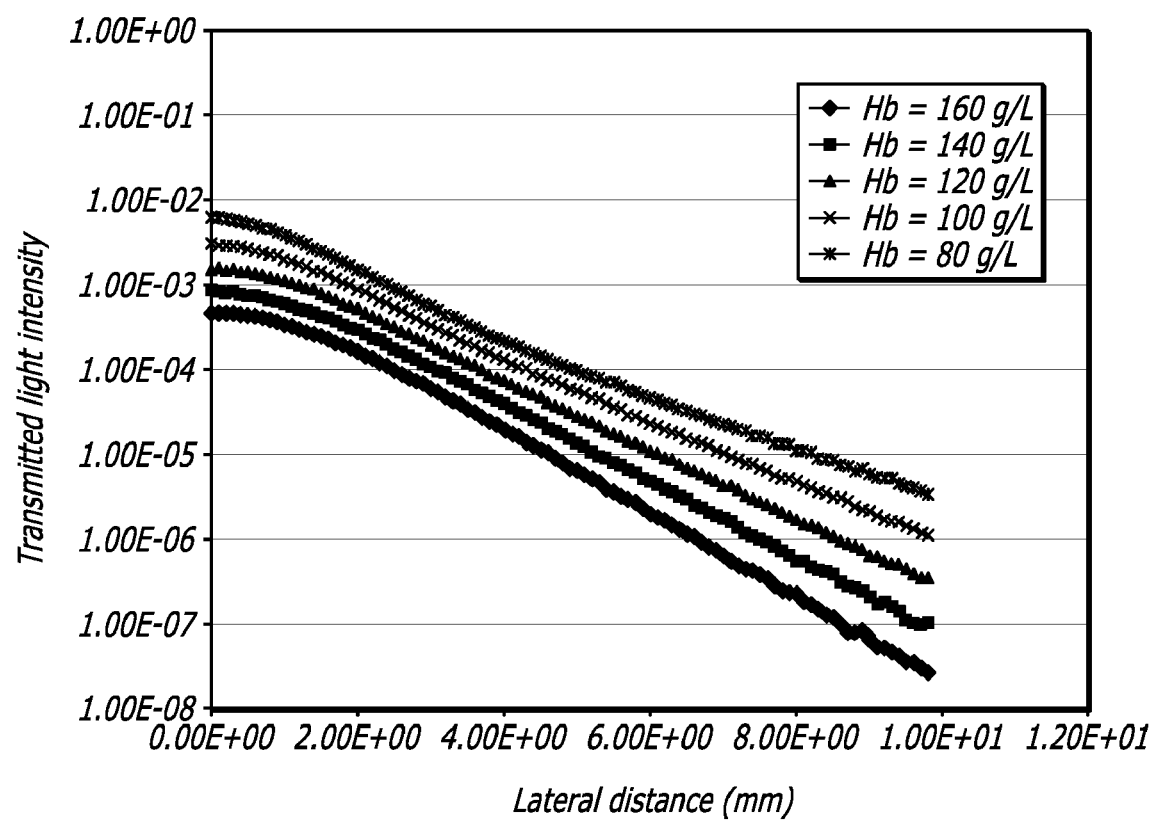

FIGS. 14*a-c* present graphs of typical light intensity profiles for the back-fluorescence, transmittance, and reflectance signals, for a blood ICG concentration of $5 \times 10^{-4}$ μg/μL. All the results are normalized to an incident light intensity of 1.

The graph of FIG. 14a presents the back-fluorescence intensity decreases at all distances when the blood hemoglobin content increases. As the blood hemoglobin content increases, the fluorescent light is absorbed more intensely and the back-fluorescence decreases. This is the effect that prevents us from using the same calibration equation between fluorescence and ICG concentration for all blood hemoglobin contents in the dialysis situation. We also note a linear dependence of the logarithm of the back-fluorescence signal as a function of lateral distance starting from 1.5 mm approximately from the point of entry.

The graph of FIG. 14b presents the reflected light intensity that is higher at short distances from the point of entry of the incident beam when the blood hemoglobin content is more elevated. At far distances from the point of entry of the incident beam, the reflected light intensity decreases when the blood hemoglobin content increases. This is interpreted considering that when the blood hemoglobin content is more elevated, light scattering is more intense. Therefore, the probability for photons to bounce out of the medium close to the point of entry is higher. Photons exiting the blood farther from the point of entry have traveled a longer distance in the blood and have been absorbed in larger amounts. The reflected light intensity decreases when absorption and scattering (blood hemoglobin content) increase. The reflected light intensity curves cross at a distance of ~1.6 mm from the point of incidence of the excitation beam. The same distance is found for the three thicknesses, all the ICG concentrations and all the hemoglobin contents tested. As for the back-fluorescence, we note a linear dependence of the logarithm of the reflected light signal as a function of lateral distance starting from 2 mm approximately from the point of entry of the incident light beam.

The graph of FIG. 14c presents the transmitted light signal decreases as the blood hemoglobin concentration increases for all distances from the direction formed by the incident beam, to reflect the increase in absorption and scattering of the medium. The transmitted light intensity is in the same range as the back-fluorescence when the medium thickness is 4.5 mm. This observation suggests that since we easily detect back-fluorescence from our blood calibration cell, we should also be able to detect light transmitted through 4.5 mm of blood (especially given that the quantum yield for fluorescence is assumed to be 1 in the simulations, vs. ~0.04 in reality). Again we note a linear dependence of the logarithm of the transmitted light signal as a function of lateral distance starting from 3 mm approximately from the point of entry of the incident light beam The graphs in this summary correspond to a blood ICG concentration of $5 \times 10^{-4}$ g/L. Similar trends noted for all ICG concentrations.

At this point, we needed to establish a calibration relationship for the back-fluorescence signal using the transmitted light. we reasoned that since the logarithm of the back-fluorescence varies linearly with lateral distance and the logarithm of the transmitted light varies linearly with lateral distance, the two quantities should vary linearly as a function of each other. Furthermore, the back-fluorescence intensity varies linearly with blood ICG concentration up to ICG concentrations of ~$10^{-3}$ as previous simulations and empiric results have abundantly established. Consequently, the logarithm of the back-fluorescence intensity should vary linearly with the logarithm of the blood ICG concentration. Combining the two propositions, we would expect that the logarithm of the back-fluorescence satisfies a multiple linear relationship with the logarithm of the transmitted light and the logarithm of the ICG concentration.

The optical signals have been integrated (summed) over defined distance intervals from the point of entry and have performed multiple linear regression analyses considering the logarithm of the back-fluorescence signal as the dependent variable and the logarithm of the transmitted light and the logarithm of the ICG concentration as the independent variables (See results in Table 1).

TABLE 1

| Linear regression analysis | Model 1: optical signals integrated between 2.1 and 4 mm | Model 2: optical signals integrated between 0.2 and 2 mm (T starts at 0 mm) | Model 3: optical signals integrated between 0.5 and 2 mm (T starts at 0 mm) |
|---|---|---|---|
| Coefficient of variation $R^2$ | 0.999 | 0.999 | 0.999 |
| Constant | 1.113 | 1.474 | 1.080 |
| Concentration Coefficient | 0.968 | 0.980 | 0.972 |
| Transmitted light coefficient | 0.516 | 0.189 | 0.198 |

The results show that the multiple linear relationships may account very well for the variations of the back-fluorescence signal ($R^2 > 0.999$). The coefficient of the concentration term is nearly 1, suggesting that there is a one-to-one correspondence between the back-fluorescence intensity and blood ICG concentration, once the increased opacity of the blood with increasing ICG concentration and blood hemoglobin concentration are accounted for by a decrease of the transmitted light signal. The coefficient associated with the transmitted light signal increases when the intensity of the transmitted signal decreases because of sampling farther away from the illumination axis. Measuring the optical signals near or far from the direction of entry of the light does not affect the quality of the fit or the partial one-to-one dependence of the back-fluorescence signal on blood ICG concentration.

Figure 15A:
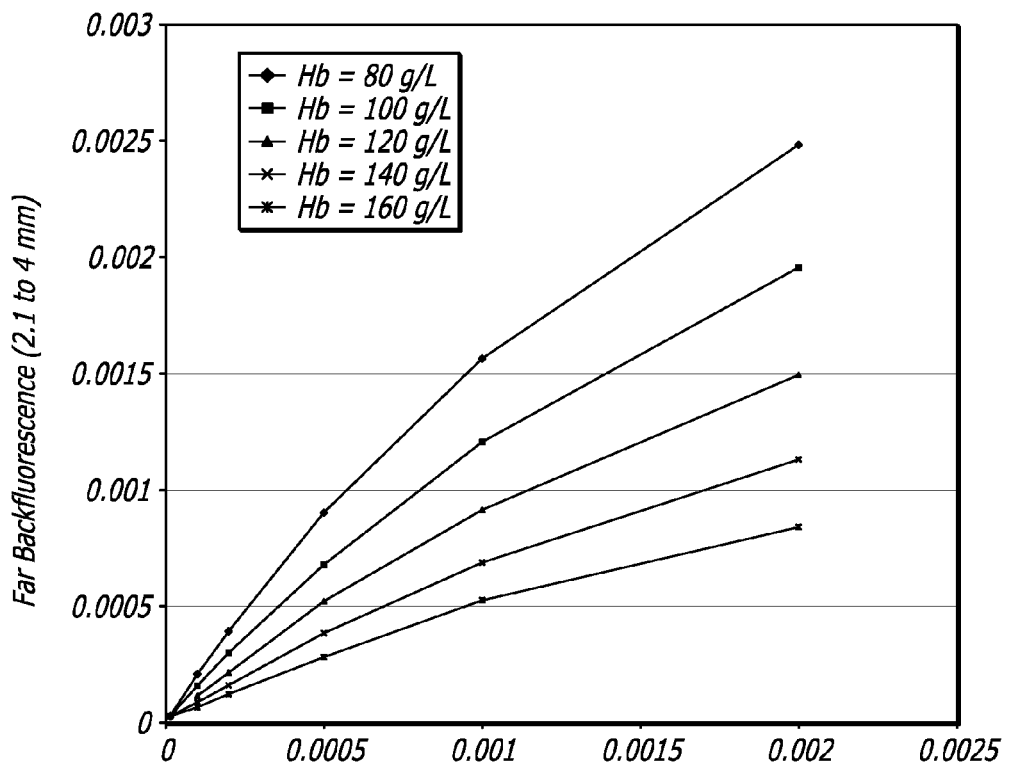
FIGS. 15A-D illustrate the plots the far back-fluorescence, far transmittance, near back-fluorescence and near transmittance signals, respectively, relative to the ICG concentration.
Figure 15B:
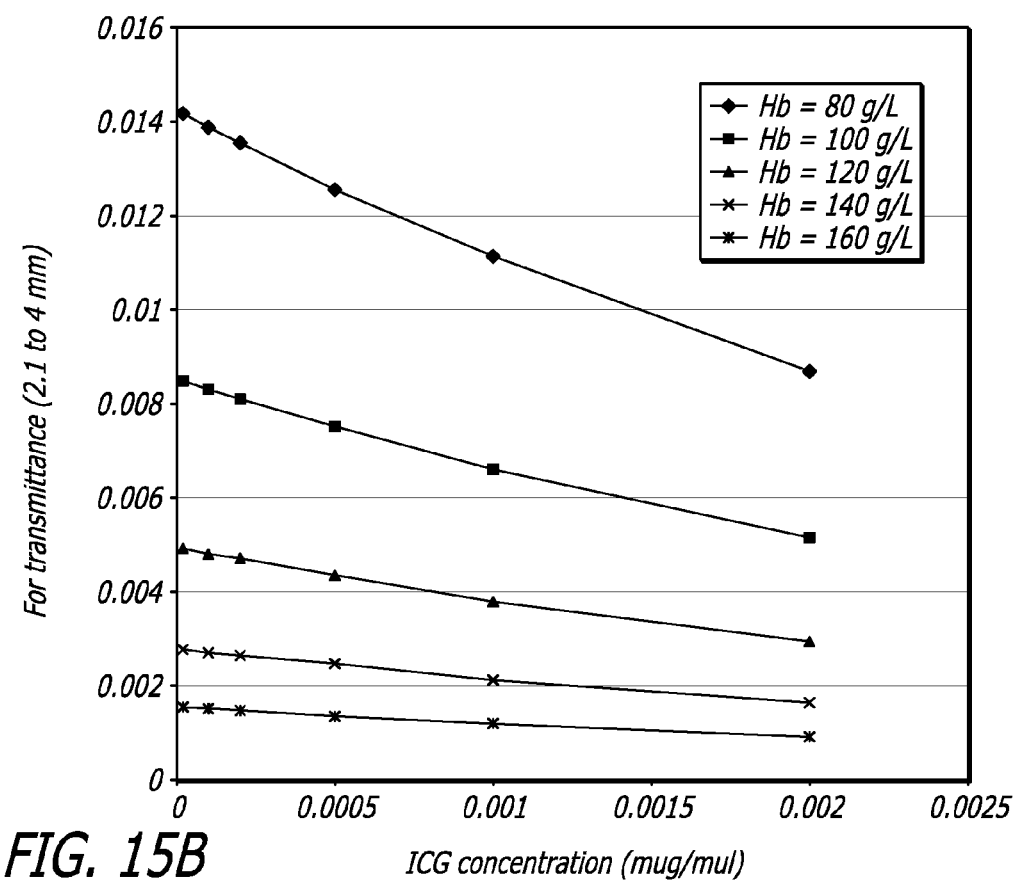
Figure 15C:
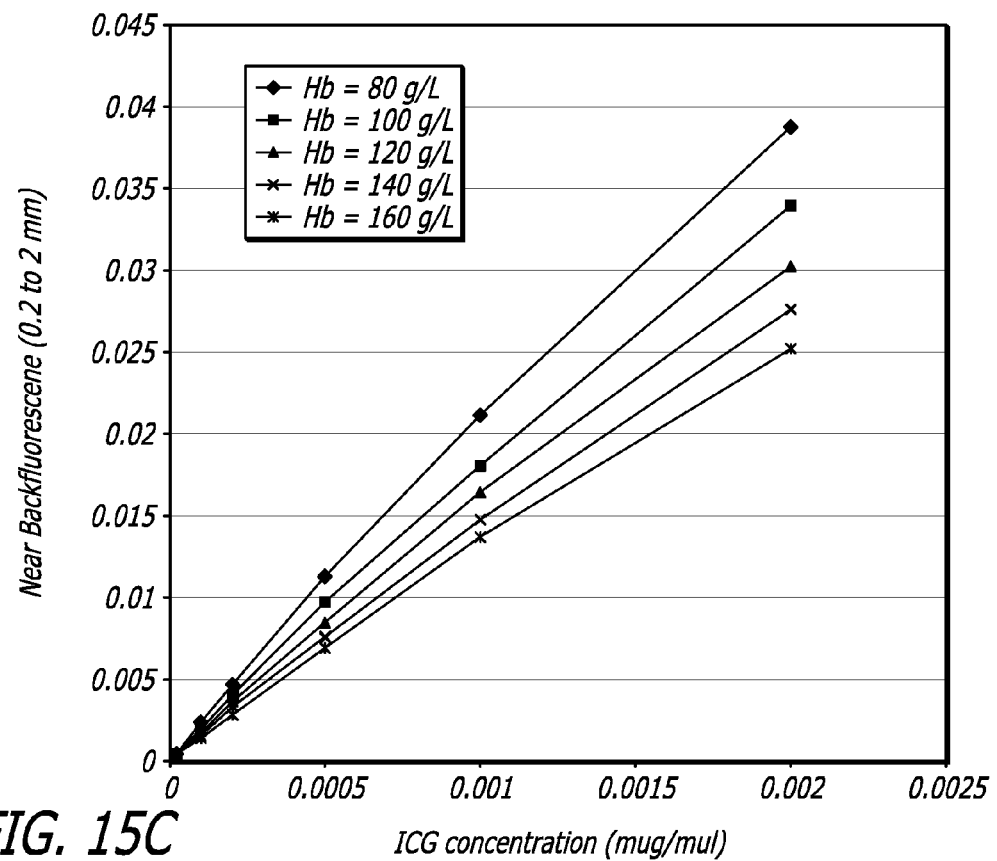
Figure 15D:
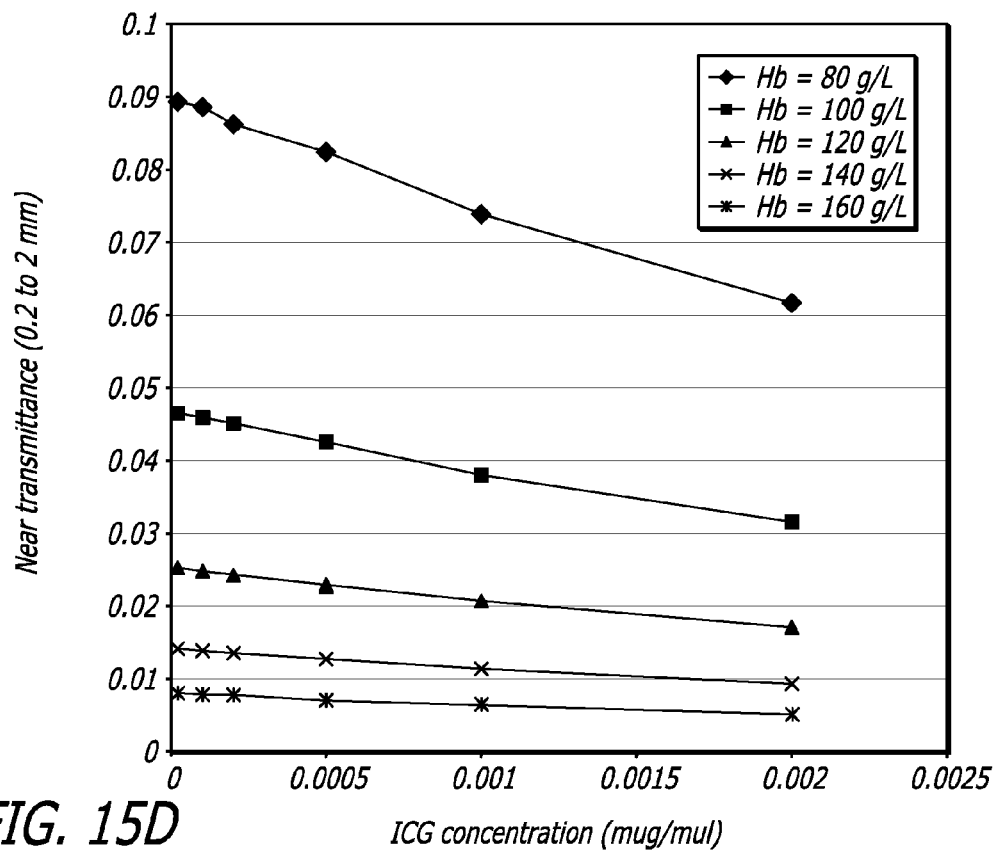

The graphs of FIGS. 15a-b show the dependence of the back-fluorescence and transmittance signals measured far away from the point of entry of the excitation light as a function of blood ICG concentration (model 1). Note that the back-fluorescence does not depend linearly on blood ICG concentration on the plot. The decrease of the transmitted light intensity with increasing blood ICG concentration acts as a correction factor which makes the linear coefficient of the ICG concentration term near 1 in the multiple linear regression analysis. Intuitively, the increase of the back-fluorescence signal intensity is not linear for elevated blood ICG concentrations because fluorescent light at 830 nm is absorbed in part by the ICG dye in the blood. The ICG dye also absorbs light at the wavelength of excitation (784 nm) which emerges across the slab and is measured as transmitted light. Because the optical properties of blood (absorption and scattering coefficients) and the absorption coefficient of ICG are similar at these two wavelengths, the effect of ICG on light transport at 830 nm and at 784 nm are similar. The absorption of the transmitted signal associated with blood ICG concentration can be used to account for the absorption of the back-fluorescence intensity with blood ICG concentration.

The traces of FIG. 14c present the back-fluorescence signal emerging near the point of entry of the light (model 2). Note that the traces appear a little more linear than those measured for a larger distance from the point of entry of the light (model 1). The effect of the blood hemoglobin content is less acute for near distances when compared to far distances of detection. The fluorescence signal intensity is about 15 times larger. Thus, there are several advantages to placing the detector measuring the back-fluorescence signal as close as possible to the incident beam.

The near transmittance signal in FIG. 14d shows similar variations to those of the far transmittance signals with respect to blood hemoglobin concentration and ICG concentration, while being approximately 5-6 times more intense than the transmittance measured away from the direction of the incident beam.

Next, we need to establish a calibration relationship for the back-fluorescence signal using the reflected light. The reasoning presented in regard to the transmitted light also applies to the reflected light. We can expect a linear dependence of the logarithm of the back-fluorescence on the logarithm of the concentration and that of the reflected light intensity. As above, we integrated (summed) the optical signals over defined distance intervals from the point of entry and performed multiple linear regression analyses considering the logarithm of the back-fluorescence signal as the dependent variable and the logarithm of the reflected light and the logarithm of the ICG concentration as the independent variables. Three situations were tested.

TABLE 2

| Linear regression analysis | Model 4: optical signals integrated between 2.1 and 4 mm | Model 5: optical signals integrated between 0.2 and 2 mm | Model 6: back-fluo integrated between 0.5 and 2 mm, R between 2.1 and 4 mm |
|---|---|---|---|
| Coefficient of variation $R^2$ | 0.999 | 0.999 | 0.999 |
| Constant | 4.668 | −0.082 | 2.764 |
| Concentration Coefficient | 1.075 | 0.936 | 1.022 |
| Reflected light coefficient | 1.975 | −0.974 | 0.820 |

We note that the coefficient of the concentration term in the multiple linear regressions is near 1. This suggests a one-to-one dependence of the back-fluorescence signal on blood ICG concentration, once the self-absorption of the fluorescence by ICG is accounted for by the variation of the reflected light. In addition, the coefficient of the reflected light is >0 when the reflected light is measured far from the point of entry of the light beam. Conversely, the coefficient of the reflected light is <0 when the reflected light is measured near the point of entry of the light beam. This result is consistent with the observation made earlier that the reflected light intensity increases near the point of entry whereas the reflected light intensity decreases away from the point of entry when hemoglobin increases (the back-fluorescence decreases for all distances when hemoglobin increases).

Based on these results, an alternate approach to account for the effect of blood hemoglobin content of the relationship between blood ICG concentration and back-fluorescence is to measure the reflected light intensity. Naturally, simultaneous measurement of the reflected and transmitted light could further specify the correction factors to use and account for this effect.

Next, we need to select of a correction approach. Using the coefficients derived from the multiple linear regression models, we compared the "experimental" back-fluorescence intensities for the different situations of the model with those predicted by the linear regression analyses.

TABLE 3

|  | Model 1 | Model 2 | Model 3 |
|---|---|---|---|
| Mean relative error magnitude | 2.95% | 1.96% | 2.70% |
| Peak relative error magnitude | 10.2% | 4.28% | 7.84% |

|  | Model 4 | Model 5 | Model 6 |
|---|---|---|---|
| Mean relative error magnitude | 8.36% | 4.67% | 4.40% |
| Peak relative error magnitude | 23.23% | 11.7% | 10.92% |

Figure 16:
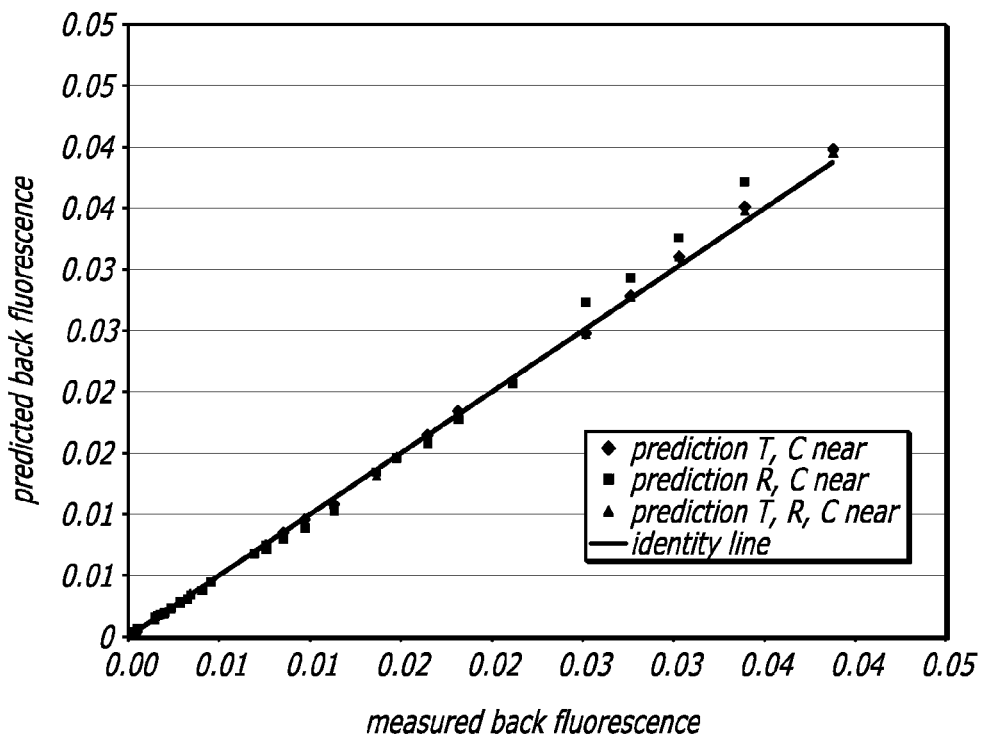
FIG. 16 illustrates the plot of predicted back-fluorescence vs. measured back-fluorescence.

The graph of FIG. 16 shows the back-fluorescence predicted by models 2 and 5 as a function of the experimental back-fluorescence. The tabulated results and the plot suggest that the correction approach that uses the transmitted light intensity is more effective at accounting for the changes of the optical properties of the medium associated with the blood hemoglobin content changes than the approach that uses reflected light, especially for the higher back-fluorescence intensities (i.e. ICG concentrations). This must be weighed against the fact that the reflected light is far more intense than the transmitted light and potentially easier to measure with respect to the probe design. Using both the transmitted and reflected light signals (yellow dots) improves the quality of the fit only marginally.

The calibration equation for model 2 reads:

$$C = 10^{-1.505} \cdot T^{-0.192} \cdot BF^{1.02}$$

Figure 17:
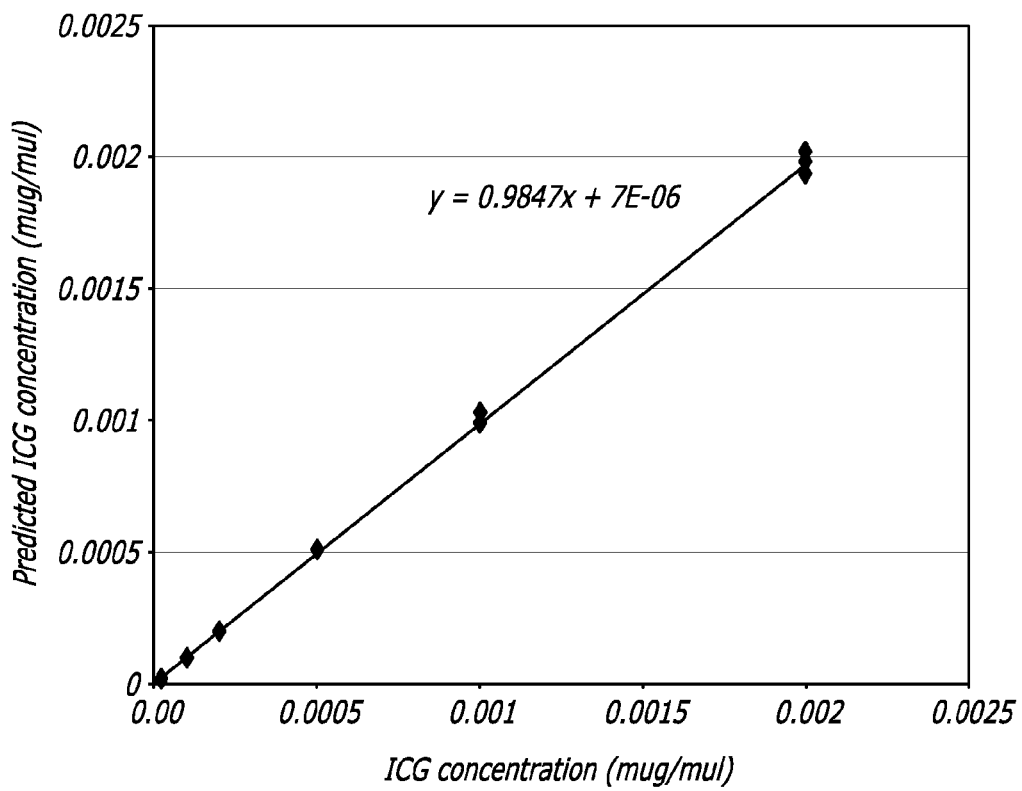
FIG. 17 illustrate the plot of the predicted ICG concentration vs. the true ICG concentration.

The relative error between predicted and real ICG concentrations=abs(C-predicted C)/C averages 0.02 and has a maximum value of 0.046 over the whole range of ICG concentrations and blood hemoglobin concentrations. The graph of FIG. 17 shows the predicted ICG concentration as a function of the true ICG concentration over the range of concentrations tested.

The results above indicate that it is possible to derive a single relationship to express the blood ICG concentration as a function of the back-fluorescence intensity and transmitted light intensity. The form of the relationship is as follows:

$$C_{ICG} = A \cdot T^{\alpha} \cdot B_{Fluo} \text{ and } C_{ICG} = K \cdot R^{\gamma} \cdot B_{Fluo}$$

where $C_{ICG}$ is the blood ICG concentration, $B_{Fluo}$ represents the back-fluorescence intensity and T and R are the transmitted and reflected light intensities, respectively. Parameters A, K, $\alpha$ and $\gamma$ are constants to be determined experimentally.

In addition to the above findings the study also indicated that it is possible to derive another relationship to express the blood ICG concentration such as the ICG concentration as a function of a forward-fluorescence intensity detected across the thickness of the tube and the transmitted or reflected light emitted from the medium carrying the indicator as follows:

$$C_{ICG} = B \cdot T^{\beta} \cdot F_{Flou} \text{ and } C_{ICG} = K \cdot R^{\gamma} \cdot F_{Fluo}$$

where $C_{ICG}$ is the blood ICG concentration, $F_{Fluo}$ represents the forward fluorescence intensity, T is the transmitted light intensity and the R is the reflected light intensity. Parameters B, K, $\beta$, $\gamma$ are constants to be determined experimentally.

Experimental Validation

Figure 18:
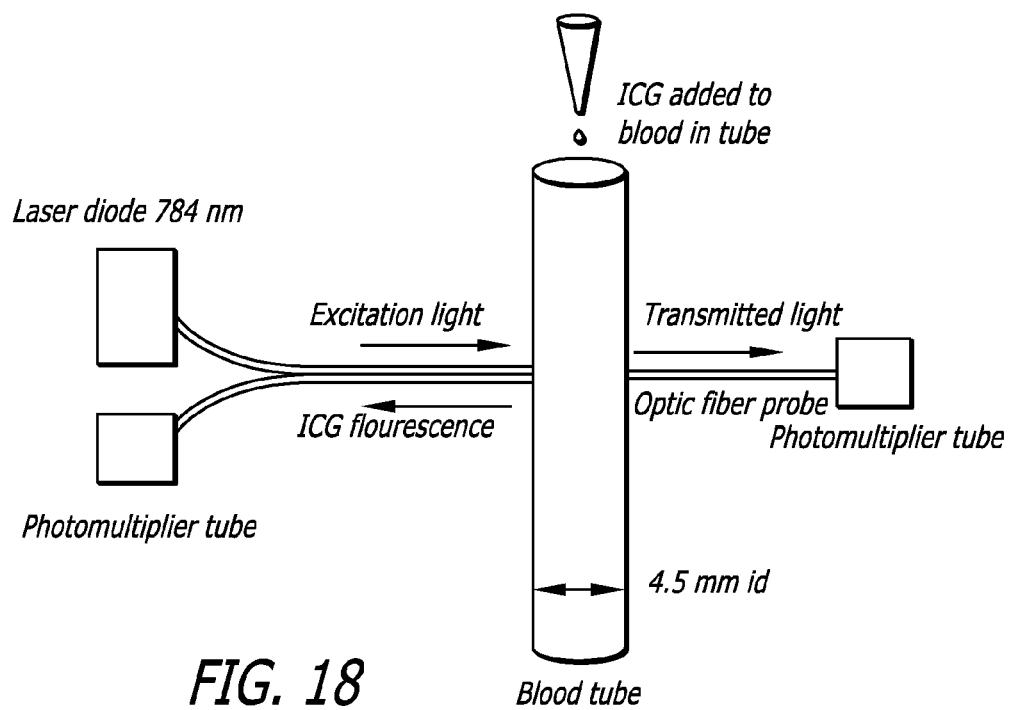
FIG. 18 is a depiction of the experimental setup used for calibration of the hemodialysis system.

The experimental validation was carried out in accordance with FIG. 18 in a segment of transparent plastic tube with diameter 4.5 mm. The tube was held snuggly in a black plastic holder in which two optical fiber probes were inserted perpendicular to the tube. The excitation/back-fluorescence probe was made of one 400 micron excitation glass fiber surrounded by six 400 micron fibers used to measure the back-fluorescence remitted by blood in the tube. The excitation fiber was coupled to the output of a laser diode emitting at 784 nm. The back-fluorescence fibers were connected to a photomultiplier tube, whose output was amplified with a lock-in amplifier. On the opposite side, the transmitted light probe was similar to the excitation/back-fluorescence probe. The six 400 micron glass fibers were connected to a second photomultiplier tube while the central 400 micron fiber was unused.

The plastic tube was closed at the bottom with a three-way stopcock that was used to insert and mix rabbit blood to varying amounts of indocyanine green. The hematocrit of the blood was varied by mixing blood from the rabbit to either plasma or red blood cells obtained by centrifugation of a second blood sample. For each level of hematocrit, the blood ICG concentration was varied between 0 and $3 \times 10^{-3}$ μg/μl approximately. The fluorescence and transmitted light intensities were recorded after each addition of ICG.

Figure 19:
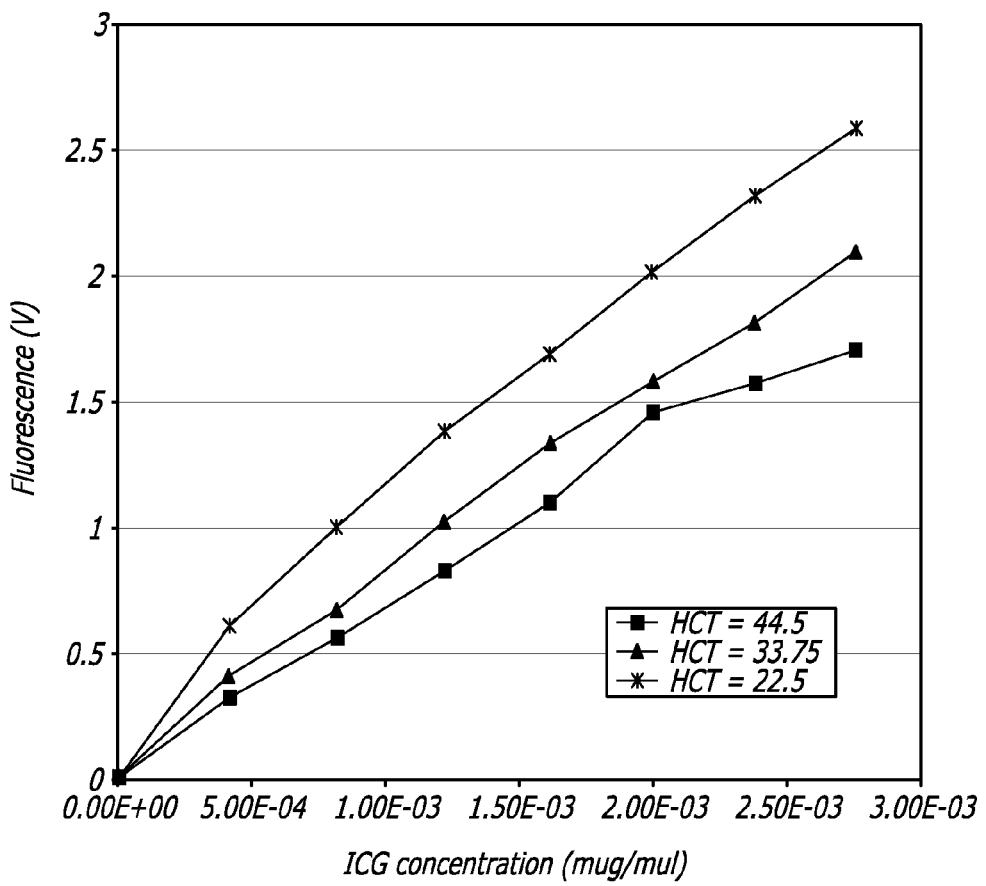
FIG. 19 is a depiction of a plot of fluorescence signal vs. ICG concentration based on multiple levels of hematocrits.

The graph of FIG. 19 shows the fluorescence recorded in one study for three levels of hematocrits. The experimental fluorescence decreases as the hematocrit increases to reflect the increased absorption of the fluorescent light by blood hemoglobin. This result is similar to that observed in the simulation study (for comparison, a hematocrit of 33.75 corresponds to a blood hemoglobin content of approximately 110 g/L)

Figure 20:
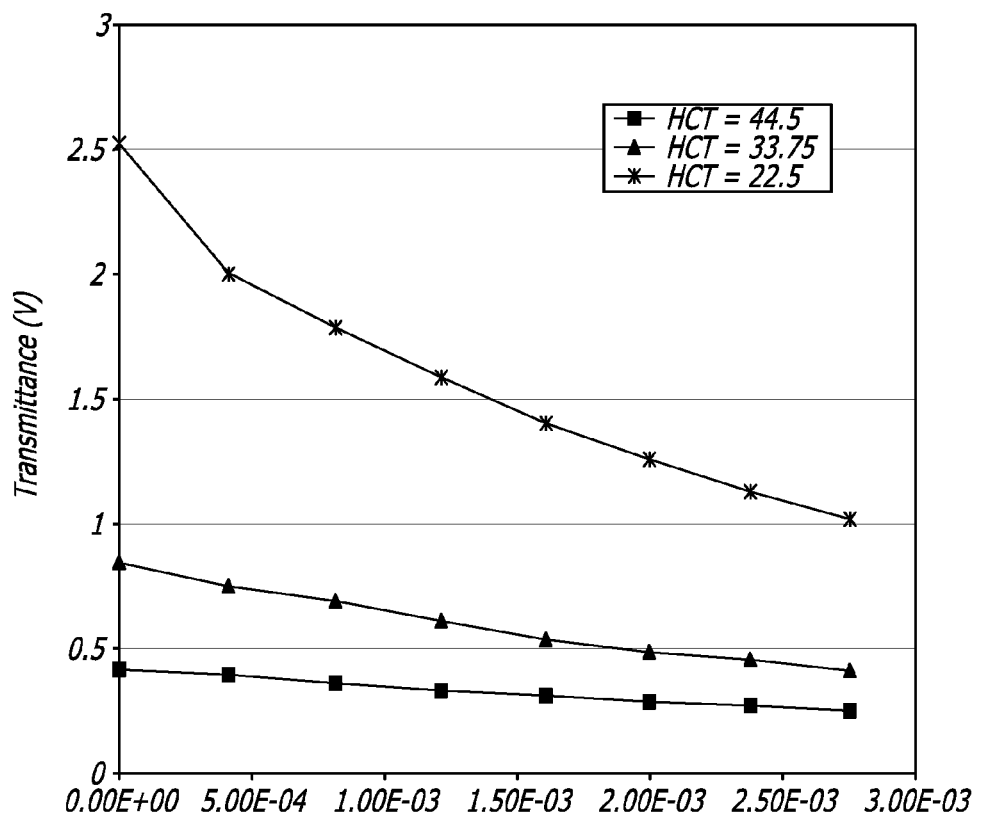
FIG. 20 is a depiction of a plot of transmittance signal vs. ICG concentration based on different levels of hematocrits.

The graph FIG. 20 shows the transmitted light intensity variations as a function of blood ICG concentration for different levels of hematocrit. Addition of ICG renders the blood more absorbent, which decreases the transmitted light. When the hematocrit is higher, the transmitted light intensity is decreased because both scattering by red blood cells and absorption by blood hemoglobin are increased. The experimental trends reflect the results of the simulation.

To validate the model, we approximated the data collected in two different experiments with the model $C_{ICG}=A \cdot T^{\alpha} \cdot B^{\beta}_{Fluo}$. Parameters A, α and β were selected by least squares approximation of the empirical data with those predicted by the model equation. The approximation yielded α=−0.26, β=0.97. Parameter β was statistically not different from 1 in agreement with the predictions from the simulation study. Parameter α had sign predicted by the simulation and a numeric value in the range predicted by the simulation study. The exact value of α depends on the area over which the transmitted light intensity is collected and other experimental factors, which could not be matched exactly in the simulation study and the experiments, hence the difference between the values predicted in the simulation and our experimental results. Note also that scaling of the transmitted light or fluorescence measurements obtained by changing the gain of an amplifier or the laser intensity only affects the coefficient A without changing the power coefficients α and β.

Figure 21:
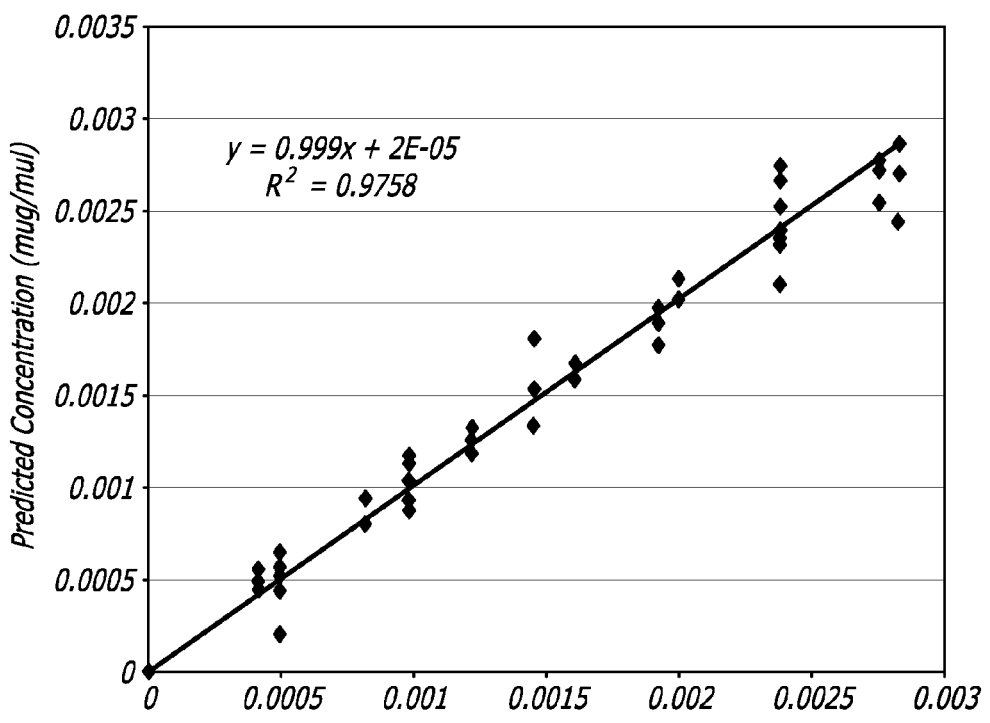
FIG. 21 is a depiction of model predicted ICG concentration vs. measured experimental ICG concentration.

The graph FIG. 21 shows the ICG concentration in blood predicted by the model as a function of the experimental ICG concentration. The regression line between the two variables is not different from the line of identity. The average quadratic error between the model prediction and the experimental ICG concentration is $10^{-4}$ μg/μl. This error corresponds to −5% of the peak concentration observed clinically during cardiac output fluorescence dilution measurements when the injected ICG dose is 1 mg.

We have established through computer simulations and verified experimentally that the ICG concentration in blood can be estimated by measuring the fluorescence intensity of the ICG and the light intensity transmitted through the container of the blood.

This calibration method can be used to calculate the ICG concentration in blood flowing through the dialyzer tube during kidney dialysis. The calibration method corrects for changes in the blood hematocrit or hemoglobin content between different subjects or within the same subject as hematocrit changes during the dialysis.

When transmitted light intensity (T) and fluorescence intensity ($B_{Fluo}$) are measured, the calibration equation is of the form $C_{ICG}=A \cdot T^{\alpha} \cdot B_{Fluo}$ where α is constant, once the conditions of measurement of the transmitted light intensity (acceptance angle, detection area) are set. Parameter A depends on experimental factors such as the intensity of the excitation light.

The computer simulations predict a similar equation $C_{ICG}=K \cdot R^{\gamma} \cdot B_{Fluo}$ when the reflected light intensity (R) and fluorescence intensity ($B_{Fluo}$) are measured. In this equation, exponent γ is constant, once the conditions of measurement of the reflected light intensity (acceptance angle, detection area) are set. Parameter K depends on experimental factors.

The simulations provide indications about the design of the probe used to measure the fluorescence and transmitted light intensities: 1) Use fibers with large acceptance angles to capture as much light as possible, 2) Measure the back-fluorescence intensity as close as possible to the point of entry of the incident light. Covering approximately a 1 mm ring around the point of entry captures the most intense back-fluorescence signal, 3) Measure the transmitted light signal over approximately a 1 mm ring across from the point of entry of the incident light beam, 4) Using a probe that measures both the transmitted and reflected light signals could further improve the quality of the correction.

These methods and systems may be utilized to measure several cardiovascular parameters. Once the system has been calibrated to the subject (where necessary) and the indicator emissions detected and recorded over time, the computing system may be used to calculate cardiovascular parameters including cardiac output and blood volume.

Cardiac Output Calculations.

In some embodiments, the cardiac output can be calculated using equations which inversely correlate the area under the first pass indicator emission curve (magnitude of intensity curve) with cardiac output. Cardiac output is typically expressed as averages (L/min). The general methods have been previously described (Geddes, supra, herein incorporated by reference).

Classically, the descending limb of the curve is plotted semi-logarithmically to identify the end of the first pass of indicator. For example, the descending limb of the curve may be extrapolated down to 1% of the maximum height of the curve. The curve can then be completed by plotting values for times preceding the end time. Finally, the area under this corrected curve is established and divided by the length (time) to render a mean height. This mean height is converted to mean concentration after calibration of the detector. The narrower the curve, the higher the cardiac output; the wider the curve, the lower the cardiac output. Several variations of this calculation method are found, including methods that fit a model equation to the ascending and descending portions of the indicator concentration curve.

Depending upon the indicator type and dosage selected, the curve may not return to zero after the end of the first pass due to a residual concentration of indicator re-circulating in the system. Subsequent calculations of cardiac output from the curve may then account for this recirculation artifact by correcting for the background emissions, prior to calculating the area under the curve.

Sequential measurements of a cardiovascular circulatory parameter, such as cardiac output or blood volume, may be taken. Each measurement may be preceded by the administration of an indicator to the cardiovascular system. Each measurement may be separated by a time period during which the indicator that was previously administered is substantially eliminated from the circulatory system, for instance by metabolic processes.

To obtain a measurement in absolute physical units, e.g., in liters per minute for cardiac output or liters for blood volume, a blood sample may be taken after each administration of the indicator for calibration purposes, as explained in more detail above.

Another approach may be to take a blood sample only after the first administration of the indicator and to use this blood sample for calibration purposes during each subsequent administration of the indicator and measurement of its resulting fluorescence. However, the operating characteristics of the test equipment may shift during these tests. The optical properties of the tissue being illuminated may also change. The positioning of the illumination source and/or the photo detector may also change. All these changes can introduce errors in the computation of the parameter in absolute physical units when the computations are based on a blood sample that was taken before the changes occurred.

These errors may be minimized by measuring the changes that occur after the blood sample is taken and by then adjusting the measured fluorescence intensity to compensate for these measured changes. This may be accomplished by measuring the intensity of the illumination light after it is transmitted through or reflected by the tissue through which the administered indicator passes. This illumination intensity measurement may be made shortly before, during or shortly after each administration of the indicator. The computations of the cardiovascular parameter that are made during tests subsequent to the first test (when the calibrating blood sample was taken) may then be adjusted in accordance with variations in these illumination intensity measurements.

For example, the computation of the cardiovascular parameter that is made following the second administration of the indicator may be multiplied by the ratio of the illumination intensity measurement made prior to the first administration of the indicator to the illumination intensity measurement made prior to the second administration of the indicator. If the illumination intensity between the first and second measurements doubles, for example, application of this formula may result in a halving of the computation. Other functional relationships between the measured cardiovascular parameter and the illumination intensity measurements may also be implemented.

Any equipment may be used to make the illumination intensity measurements. In one embodiment, the photo detector that detects the fluorescence intensity may also be used to make the illumination intensity measurements. The optical filter that removes light at the illumination frequency may be removed during the illumination intensity measurements. The leakage of the illumination thought this filter may instead be measured and used as the information for the computation.

Another approach to minimizing the number of needed blood samples for a sequence of tests is to take advantage of the known relationship between the amount of indicator that is injected, the volume of blood in the circulatory system and the resulting concentration of the indicator in that blood.

One step in this approach is to determine the volume of blood in the cardiovascular circulatory system using any technique, such as a tracer dilution technique, applied for instance with the Evans Blue dye. The concentration of the indicator after it is administered and mixed throughout the total blood volume, with no offset for metabolic elimination, may then be computed by dividing the amount of the indicator that is administered by the volume of the blood.

Figure 10:
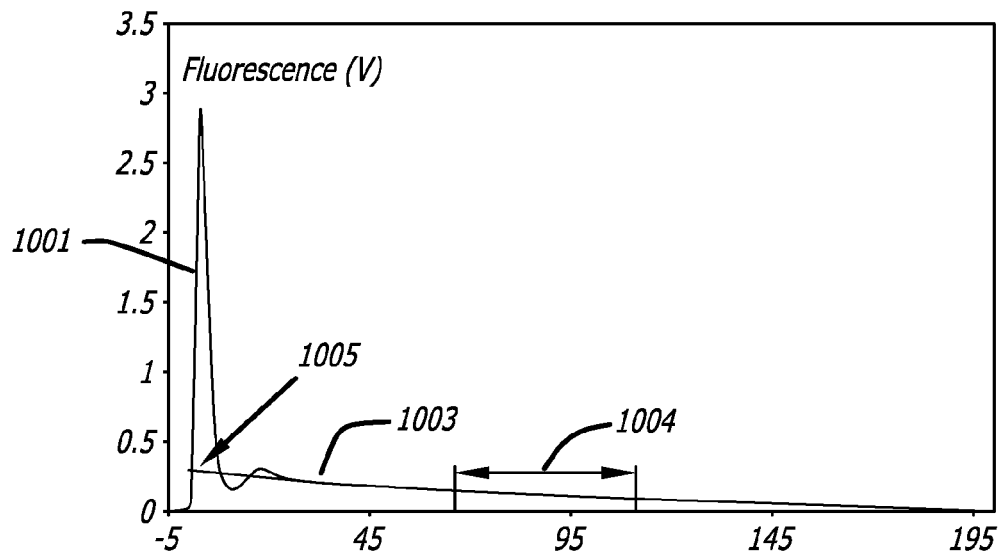
FIG. 10 illustrates a fluorescence intensity curve that includes an extrapolation that intercepts the point on the curve at which the fluorescence is indicative of the concentration of the indicator when mixed throughout the volume of blood of the subject.

The theoretical magnitude of the intensity of the fluorescence from the indicator after the indicator is mixed throughout the total blood volume, without having been metabolized or otherwise eliminated from the circulatory system, may then be determined from the fluorescence curve. FIG. 10 illustrates one way that this may be done. As shown in FIG. 10, the intensity of the fluorescence of an administered indicator will often rise quickly after the injection, as illustrated by a sharply rising portion 1001. The intensity may then decay slowly, as illustrated by a slowly falling portion 1003. A portion of the curve 1004 during the slow decay may be extrapolated until it intercepts a point 1005 on the fast rising portion. The level of the intensity of the fluorescence at the point 1005 may represent the concentration of the indicator after it is administered and mixed throughout the total blood volume, with no offset for metabolic elimination, i.e., the concentration of the indicator that was computed above.

Based on this extrapolated point, a conversion factor may then be determined that converts the measured intensity of the fluorescence to the concentration of the indicator in the cardiovascular system. The conversion factor may be determined by equating it to the ratio of the concentration of the indicator that was calculated above to the measurement of the intensity of the fluorescence at the intercepted point. The concentration of the indicator at other points on the fluorescence intensity curve shown in FIG. 10 may then be computed by multiplying the measured fluorescence intensity value by the conversion factor.

Subsequent administrations of indicator may be made and measured to monitor the cardiovascular parameter over short or long periods of time. The same computational process as is described above may be used each time to determine the absolute physical value of the desired cardiovascular parameter without having to again take a blood sample. The process may also intrinsically compensate for changes between measurements, other than changes in blood volume, such as changes in the operating characteristics of the test equipment, the optical properties of the tissue being illuminated, and/or the positioning of the illumination source and/or the photo detector.

All of the foregoing computations, as well as others, may be automatically performed by a computing system. The computing system may include any type of hardware and/or software.

Results obtained using this system can be normalized for comparison between subjects by expressing cardiac output as a function of weight (CO/body weight (L/min/kg)) or as a function of surface area (cardiac index=CO/body surface area (L/min/m$^2$)).

Blood Volume Calculations.

In some embodiments, blood volume may be measured independently or in addition to the cardiac output. General methods of measuring blood volume are known in the art. In some embodiments, circulating blood volume may be measured using a low dose of indicator which is allowed to mix within the circulatory system for a period of time selected for adequate mixing, but inadequate or the indicator to be completely metabolized. The circulating blood volume may then be calculated by back extrapolating to the instant of injection the slow metabolic disappearance phase of the concentration curve detected over time (Bloomfield, D. A. Dye curves: The theory and practice of indicator dilution. University Park Press, 1974). Alternative methods of calculation include, but are not limited to those described in U.S. Pat. No. 5,999,841, 6,230,035 or 5,776,125, herein incorporated by reference.

This method and system may be used to examine the general cardiovascular health of a subject. In one embodiment, the method may be undertaken one time, such that one cardiac output and or blood volume measurement would be obtained. In other embodiments, the method may be undertaken to obtain repeated or continuous measurements of cardiovascular parameters over time. Further, repeated measures may be taken in conditions where the cardiovascular system is challenged such that a subject's basal and challenged cardiovascular parameters can be compared. Challenges which may be utilized to alter the cardiovascular system include, but are not limited to exercise, treatment with biologically active agent which alter heart function (such as epinephrine), parasympathetic stimulation (such as vagal stimulation), injection of liquids increasing blood volume (such as colloidal plasma substitutes) or exposure to enhanced levels of respiratory gases.

Figure 1:
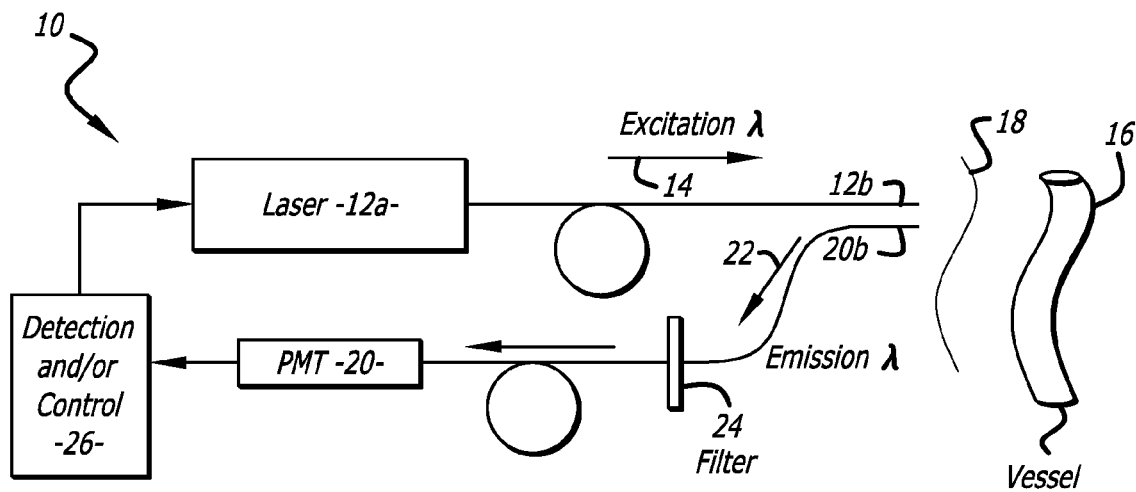
FIG. 1 is a diagrammatic depiction of an example of one embodiment of an exemplary cardiac output measurement system.
Figure 2:
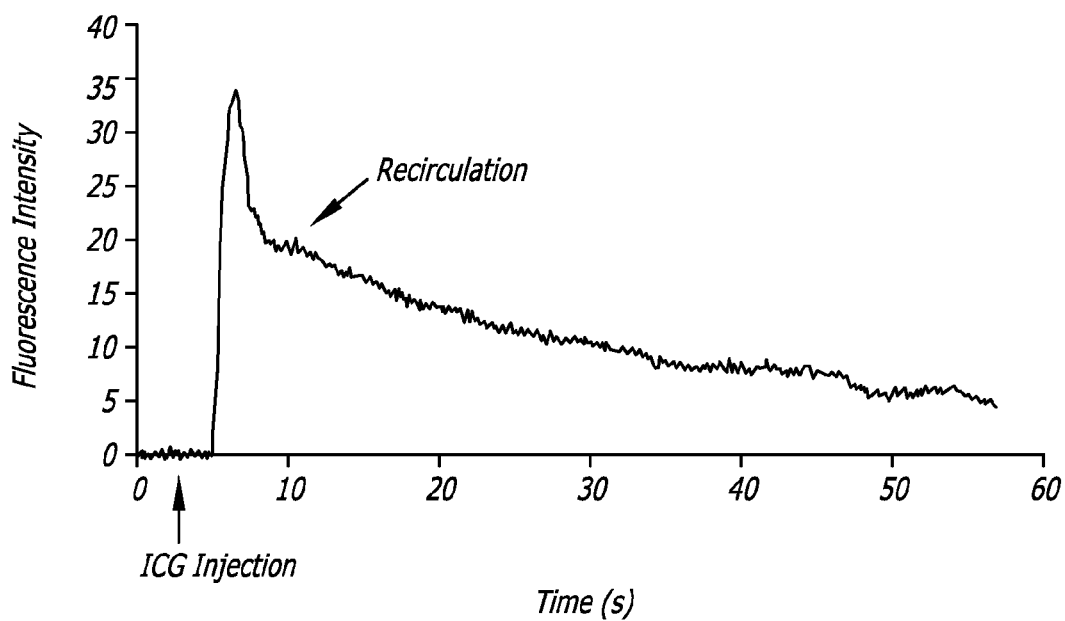
FIG. 2 is a fluorescence intensity curve generated using one embodiment of the cardiovascular measurement devices and methods.
Figure 3:
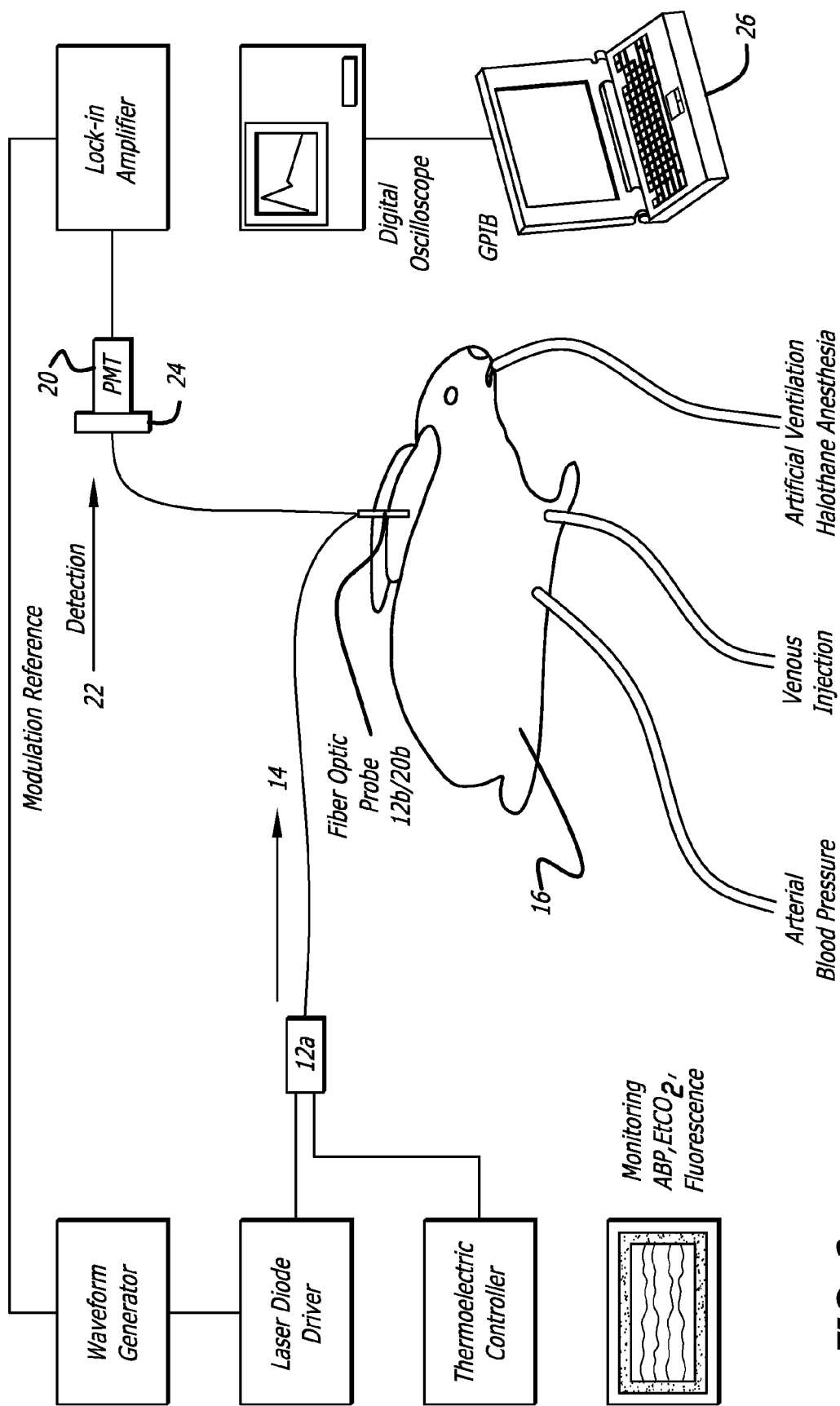
FIG. 3 is a diagrammatic depiction of an example of one embodiment of the cardiovascular measurement device having a photodetector positioned on the ear skin surface.

A schematic of one embodiment of an exemplary system 10 is shown in FIG. 1. The system comprises an illumination source 12 here a 775 nm laser selected to emit a excitation wavelength of light 14 which maximally excites ICG, the indicator selected. Here the illumination source 12 is positioned proximately to the subject 16, such that the excitation wavelength of light 14 is shone transdermally onto the indicator circulating in the bloodstream. The system also comprises a photodetector 20 placed in proximity to the subject's skin surface 18 for detection of the indicator emission wavelength 22. Optionally, a filter 24 may be used for isolating the peak wavelength at which the indicator emits, being about 830 nm. Finally, the photodetector 20 is operably connected to a microprocessor 26 for storing the electronic signals transmitted from the photodetector 20 over time, and generating the indicator concentration curve (FIG. 2). Optionally, the microprocessor 26 may regulate the illumination source to coordinate the excitation and detection of emissions from the indicator, for example using a modulation technique. The microprocessor may also comprise software programs for analyzing the output obtained from the detector 20 such that the information could be converted into values of cardiac output or blood volume, for example and/or displayed in the form of a user interface.

In order to demonstrate the utility of cardiovascular measurement devices and methods, a non-invasive indicator detection system 10 was used to repeatedly monitor cardiac output. With reference to FIG. 1, a fiber optic 12b transmitted light from illumination source 12a to the subject's skin 18. A second fiber optic 20b, positioned near the skin 18 transmitted the emitted light to a photodetector 20. The indicator was intravenously injected. A body portion which included blood vessels near the surface of the skin was irradiated with a laser. A characteristic fluorescence intensity/concentration curve was obtained upon excitation with laser light at about 775 nm and detection of the fluorescence at about 830 nm. From this information cardiac output and blood volume for the subject was calculated.

The system used for this method may comprise a variety of additional components. For example, non-invasive detection is described for monitoring of indicators within the circulatory system of the patient. Modifications of the detectors to accommodate to various regions of the patient's body or to provide thermal, electrical or chemical stimulation to the body are envisioned within the scope of cardiovascular measurement devices and methods. Also, calibration of the system may be automated by a computing system, such that a blood sample is drawn from the patient after administration of the indicator, concentration detected and compared with known standards and/or the emission curve. Also, software may be used in conjunction with the microprocessor to aid in altering parameters of any of the components of the system or effectuating the calculations of the cardiovascular parameters being measured. Further, software may be used to display these results to a user by way of a digital display, personal computer or the like.

Hemodialysis Applications.

In an exemplary embodiment, the measurement of the fluorescence dilution trace may be performed by placing the illumination and detection probe on the skin surface at the level of the AV fistula or AV shunt, on the proximal side of the fistula or shunt. Injection of the fluorescent dye may be performed through a fine needle inserted at the distal end of the fistula in venous blood returning toward the right heart. The abundant blood flow through the fistula or shunt carries the dye toward the central circulation where it mixes and gives rise to dye dilution profile that can be detected by illuminating the dye transcutaneously at an appropriate wavelength to excite its fluorescence. Analysis of the fluorescence dilution profile may be performed to estimate the cardiac output and circulating blood volume. This procedure can be operated before, during, and/or after the dialysis procedure without delaying or compromising the procedure. The patient may be monitored during the hemodialysis procedure by comparing the estimated parameters (i.e. cardiac output or circulating blood volume) to the parameters obtained before the procedure. This way the rate of fluid removal from the patient can be controlled if for example any one of cardiac output or circulating blood volume parameters changes significantly. If the measurement is performed during the dialysis procedure with blood flowing through the dialyzer, the estimated volume can include that of the blood compartment in the dialyzer, which may be subtracted to determine the patient's circulating blood volume. Cardiac output, which can be estimated from the first pass dilution curve, may not depend on whether the test is performed during the dialysis procedure.

In another exemplary embodiment, the illumination and detection probe may be attached on the external wall of the transparent tubing transporting blood from the artery to the dialyzer, or alternatively attached to the wall of a special fitting that inserts on the blood path from the patient's artery to the dialyzer as configured in an alternative embodiment of FIGS. 22A-C. Injection of the dye in the venous blood stream may be performed through a side port in the venous connection returning the dialyzed blood to the patient, through a fine needle inserted in the AV fistula or shunt or through a catheter inserted in another vein of the subject, for instance the antecubital vein. FIG. 22A represents the front view of the hemodialysis probe. The probe includes the probe body 2209 and the communication module 2201. The tubing 2207 having blood running out of the patient's body into the dialyzer is illuminated through the line 2202 by laser illumination. The lines 2203 and 2204 represent back-fluorescence intensity and reflected light intensity, respectively. The lines 2205 and 2206 represent the forward-fluorescence and transmitted light, respectively. FIGS. 22B and 22C represent the oblique and side views, respectively, of the probe. The communication module 2201 controls the illumination and receiving of emitted light intensities.

Such implementations may simplify the calibration procedure, which can be performed in-vitro in a blood loop system to characterize the light transmission and fluorescence detection characteristics of the fittings as discussed above with respect to the non-invasive calibration. While the probe configuration is presented as shown in FIGS. 22A-C and discussed above, applicant's probe is not limited to the probe of FIGS. 22A-C. Alternative embodiments of the probe's configurations are within the scope of the applicant's invention. An ordinary practitioner in this field would use the most appropriate configuration of the probe for a given application.

As discussed above the following relationships together or interchangeably can be used to determine the ICG concentration of blood during hemodialysis procedure:

$$C_{ICG}=A \cdot T^{\alpha} \cdot B_{Fluo} \text{ and } C_{ICG}=K \cdot R^{\gamma} \cdot B_{Fluo}$$

where $C_{ICG}$ is the blood ICG concentration, $B_{Fluo}$ represents the back-fluorescence intensity and T and R are the transmitted and reflected light intensities, respectively, and parameters A, K, $\alpha$, $\gamma$ are constants that are determined experimentally; and the relationships:

$$C_{ICG}=B \cdot T^{\beta} \cdot F_{Fluo} \text{ and } C_{ICG}=K \cdot R^{\gamma} \cdot F_{Fluo}$$

where $C_{ICG}$ is the blood ICG concentration, $F_{Fluo}$ represents the forward fluorescence intensity, T is the transmitted light intensity and the R is the reflected light intensity and the parameters B, K, $\beta$, $\gamma$ are constants that are determined experimentally.

This implementation may also provide an improved signal-to-noise ratio since there is no attenuation of the excitation light and fluorescence by biologic tissue. As a result, the amount of injected ICG can be reduced several fold compared to that used for detection through the skin in humans (typically 1 mg or larger). As a result, the measurements of cardiac output can be repeated frequently (~5 min) after the dye is metabolized by the liver.

Typically, more than 95% of ICG injected in the bloodstream binds to blood proteins such that the protein-bound ICG is not cleared by the dialysis procedure. Unbound ICG (MW 775) is too large to be efficiently cleared by the dialyzer. Thus, there may be no artifact or impediment in implementing such measurements during dialysis.

Furthermore, the venous injection of the ICG could be made through any large peripheral vein and does not necessarily have to be at the venous side of the AV fistula. Likewise, detection of the fluorescence dilution trace does not necessarily have to take place at the level of the AV fistula or shunt, and may occur at any site on the body surface (such as the ear lobe or the wing of the nose) if the site is well perfused and/or arterialized by local heating.

The utility of the cardiovascular measurement devices and methods is further illustrated by the following examples, which are not intended to be limiting.

Example 1

Experimental system and method. An implementation of the system and method of the cardiovascular measurement devices and methods was tested in rats. The excitation source was a 775 nm pulsed diode laser and the fluorescence was detected with a detector being a photomultiplier (PMT) with extended response in the near-infrared range of the spectrum (FIG. 1). Optic fibers were placed in close contact with the skin of the animal's ear for the excitation and detection of the indicator within the blood stream. After injection of a 100 µl bolus of ICG (0.0075 mg/ml) into the jugular vein of a rat, the fluorescence intensity trace (indicator concentration recording) was measured transcutaneously at the level of the rat's ear using reflection mode detection of emissions (FIG. 2).

Calculation of Blood Volume and Cardiac Output.

The initial rapid rise and rapid decay segments of the fluorescence intensity trace represent the first pass of the fluorescent indicator in the arterial vasculature of the animal. Such a waveform is characteristic of indicator dilution techniques. This portion of the recording is analyzed with one of several known algorithms (i.e. Stewart Hamilton technique) to compute the "area under the curve" of the fluorescence intensity trace while excluding the recirculation artifact. Here, the initial portion of the fluorescence trace y(t) was fitted with a model equation $y(t)=y_0 t^{\alpha} \exp(-\beta t)$ which approximates both the rising and descending segments of the trace. This equation derived from a "tank-in-series" representation of the cardiovascular system has been found fit well the experimental indicator dilution recordings. The numerical parameters of the fit were determined from the approximation procedure, and then the "area under the curve" was computed by numeric integration and used to find the cardiac output with the known formula:

$$Q = \frac{m}{\int_0^{\infty} C(t)\,dt} = \frac{\text{amount injected}}{\text{area under the curve}}$$

Back extrapolation of the slow decay segment of the fluorescence intensity trace to the instant when ICG is first detected in the blood (time 0) yields the estimated concentration of ICG mixed in the whole circulating blood volume. By dividing the amount of injected ICG by this extrapolated ICG concentration at time 0, the circulating blood volume was computed.

Calibration methods. Indicator concentration C(t) was computed from the fluorescence y(t) using one of two calibration methods. Transcutaneous in vivo fluorescence was calibrated with respect to absolute blood concentrations of ICG, using a few blood samples withdrawn from a peripheral artery after bolus dye injection of ICG. The blood samples were placed in a fluorescence cell and inserted in a tabletop fluorometer for measurement of their fluorescence emission. The fluorescence readings were converted into ICG concentrations using a standard calibration curve established by measuring with the tabletop fluorometer the fluorescence of blood samples containing known concentrations of ICG.

An alternative calibration procedure which avoids blood loss uses a syringe outfitted with a light excitation—fluorescence detection assembly. The syringe assembly was calibrated once before the cardiac output measurements by measuring ICG fluorescence in the syringe for different concentrations of ICG dye in blood contained in the barrel of the syringe. During the measurement of cardiac output, a blood sample was pulled in the syringe during the slow decay phase of the fluorescence trace, that is the phase during which re-circulating dye is homogeneously mixed in the whole blood volume and is being slowly metabolized. The fluorescence of that sample was converted to concentration using the syringe calibration curve and then related to the transcutaneous fluorescence reading. So long as the ICG concentrations in blood remain sufficiently low (<0.001 mg/ml), a linear relationship can be used to relate fluorescence intensity to concentration.

Either one of these calibration methods can be developed on a reference group of subjects to produce a calibration monogram that would serve for all other subjects with similar physical characteristics (i.e., adults, small children etc.). This is advantageous over prior methods at least in that an additional independent measurement of the blood hemoglobin concentration for computation of the light absorption due to hemoglobin is not required.

Example 2

Figure 4:
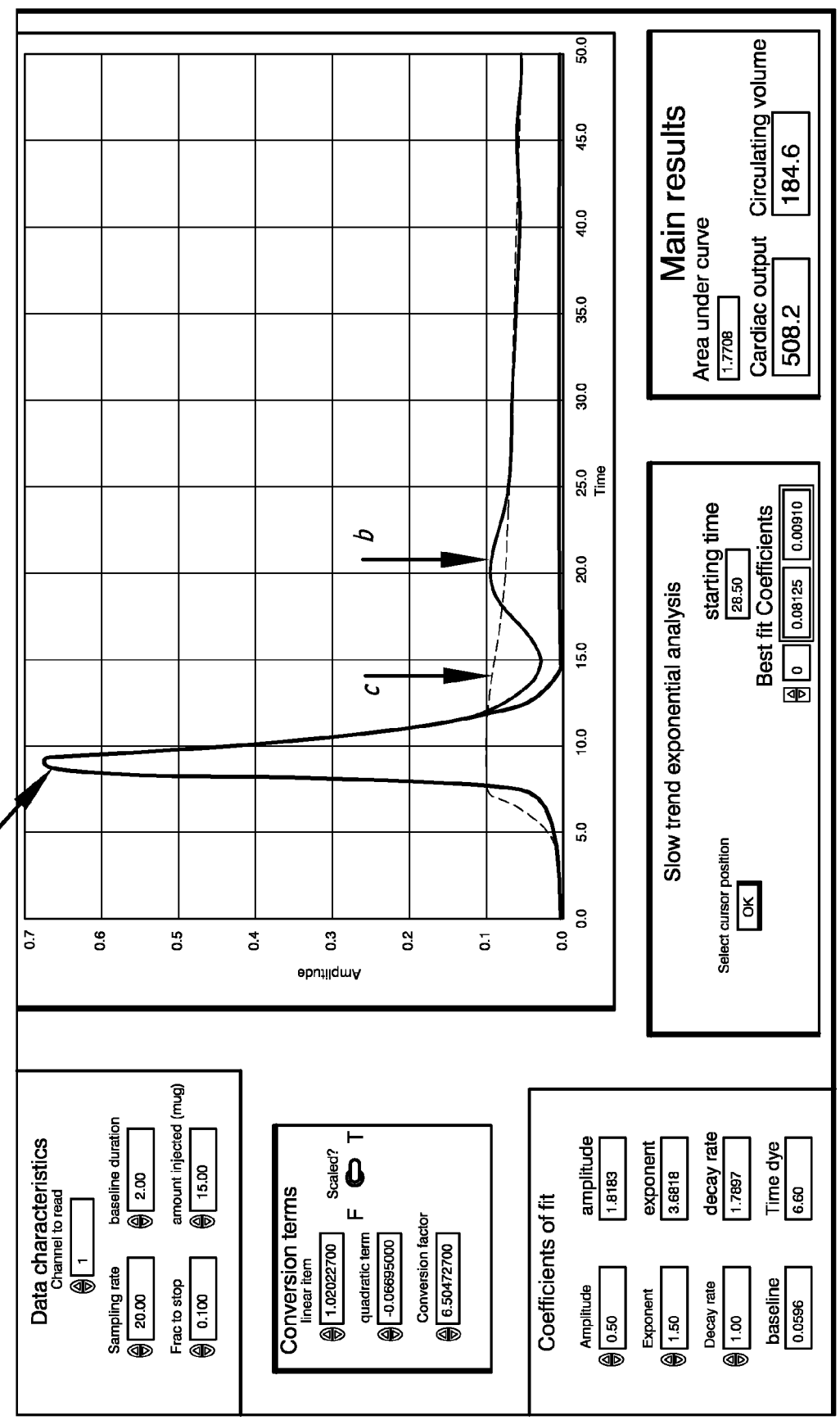
FIG. 4 is a diagrammatic depiction of a user interface of a cardiac output computer program. The interface may depict information regarding values measured and converted from fluorescence to concentration, and parameters of the curve fit for the values obtained using the method or system.

A. A sample method and system for measuring cardiac output and blood volume. Experiments have been performed in New Zealand White rabbits (2.8-3.5 Kg) anesthetized with halothane and artificially ventilated with an oxygen-enriched gas mixture ($Fio_2$~0.4) to achieve a $Sao_2$ above 99% and an end-tidal $CO_2$ between 28 and 32 mm Hg (FIG. 4). The left femoral artery was cannulated for measurement of the arterial blood pressure throughout the procedure. A small catheter was positioned in the left brachial vein to inject the indicator, ICG. Body temperature was maintained with a heat lamp.

Excitation of the ICG fluorescence was achieved with a 780 nm laser (LD head: Microlaser systems SRT-F780S-12) whose output was sinusoidally modulated at 2.8 KHz by modulation of the diode current at the level of the laser diode driver diode (LD Driver: Microlaser Systems CP 200) and operably connected to a thermoelectric controller (Microlaser Systems: CT15W). The near-infrared light output was forwarded to the animal preparation with a fiber optic bundle terminated by a waterproof excitation-detection probe. The fluorescence emitted by the dye in the subcutaneous vasculature was detected by the probe and directed to a 830 nm interferential filter (Optosigma 079-2230) which passed the fluorescence emission at 830±10 nm and rejected the retro-reflected excitation light at 780 nm. The fluorescence intensity was measured with a photomultiplier tube (PMT; such as Hamamatsu H7732-10MOD) connected to a lock-in amplifier (Stanford Research SR 510) for phase-sensitive detection of the fluorescence emission at the reference frequency of the modulated excitation light. The output of the lock-in amplifier was displayed on a digital storage oscilloscope and transferred to a computer for storage and analysis.

In most experiments, one excitation-detection probe was positioned on the surface of the ear arterialized by local heating. In some studies, the laser emission beam was separated in two beams with a beam splitter and directed to two measurement sites (ear skin and exposed right femoral artery). Two detection systems (PMT+lock in amplifier) were used for measurement of the fluorescence dilution traces from the two sites. In all experiments, a complete record of all experimental measurements (one or two fluorescence traces, arterial blood pressure, end-tidal Co2, Doppler flow velocity) was displayed on line and stored for reference.

Calculations.

A Lab View program was used to control the oscilloscope used for sampling the fluorescence dilution curves, transfer the data from the oscilloscope to a personal computer and analyze the curves online for estimation of the cardiac output and circulating blood volume. As shown on the program user interface (FIG. 5), the measured fluorescence dilution trace (a) is converted to ICG blood (b) using the calibration parameters estimated as described in the next section of this application and fitted to a model: $C(t)=C_0 t^\alpha \exp(-\beta t)$.

The model fit is performed from the time point for which the fluorescent ICG is first detected to a point on the decaying portion of the trace that precedes the appearance of re-circulating indicator (identified from the characteristic hump after the initial peak in the experimental trace). The model equation is used to estimate the "area under the curve" for the indicator dilution trace. The theory of indicator dilution technique predicts that the area under the concentration curve is inversely proportional to the cardiac output (Q): $m/\int_0^\infty C(t)dt$.
where m is the mass amount of injected indicator and c(t) is the concentration of indicator in the arterial blood at time t. The program also fits the slow decaying phase of the measurement to a single exponential to derive the circulating blood volume from the value of the exponential fit at the time of injection. For the experimental ICG trace shown in FIG. 4, the estimated cardiac output is 509 ml/min and the circulating blood volume is 184 ml, in the expected range for a 3 Kg rabbit. This computer program is advantageous in that it improved the ability to verify that the experimental measurements are proceeding as planned or to correct without delay any measurement error or experimental malfunction.

Indicator Dosage.

In this experiment is was found that a dose of about 0.045 mg injected ICG was optimal in this animal to allow for detection of an intense fluorescence dilution curve and at the same time rapid metabolic disposal of the ICG. Further, with this small dose cardiac function measurements could be performed at about intervals of 4 minutes or less.

Detector Placement.

Defined fluorescence readings were obtained by positioning the detection probe above the skin surface proximate to an artery or above tissue, such as the ear or the paw arterialized by local heating.

B. Calibration of Transcutaneous Indicator Intensity and Circulating Indicator Concentration.

Calibration of the transcutaneous fluorescence intensity measured at the level of the animals' ear as a function of ICG concentration in blood was performed as follows. A high dose of ICG (1 mg) was injected intravenously and equilibrated homogeneously with the animal's total blood volume in about a one minute period. At equilibrium, the blood ICG concentration resulting from this high dose is several times larger than the peak ICG concentration observed during the low dose ICG injections (0.045 mg) used to measure cardiac output. In this way, a calibration curve was created that accommodated the full range of ICG concentrations observed during the cardiac function measurements.

As the liver metabolizes ICG, the blood ICG concentration decreases back to 0 in about 20 minutes. During that time period, 5 to 8 blood samples (1.5 ml) were withdrawn from the femoral artery and placed in a pre-calibrated blood cuvette. The fluorescence intensity of the blood in the cuvette was converted to a measurement of concentration using the known standard curve of fluorescence intensity versus ICG concentration established for the cuvette. ICG fluorescence was measured at the level of the ear at the exact time of the blood sample withdrawal. Because ICG is homogeneously equilibrated in the animal's blood volume, when the blood samples are withdrawn, the fluorescence intensity measured at the level of the ear corresponds directly to the ICG blood concentration at the time of the measurement and therefore the ICG concentration determined from the cuvette reading. As this example shows, transcutaneous ICG fluorescence is proportional to blood ICG concentration such that a single blood withdrawal can suffice to find the proportionality factor between the two quantities.

Figure 5:
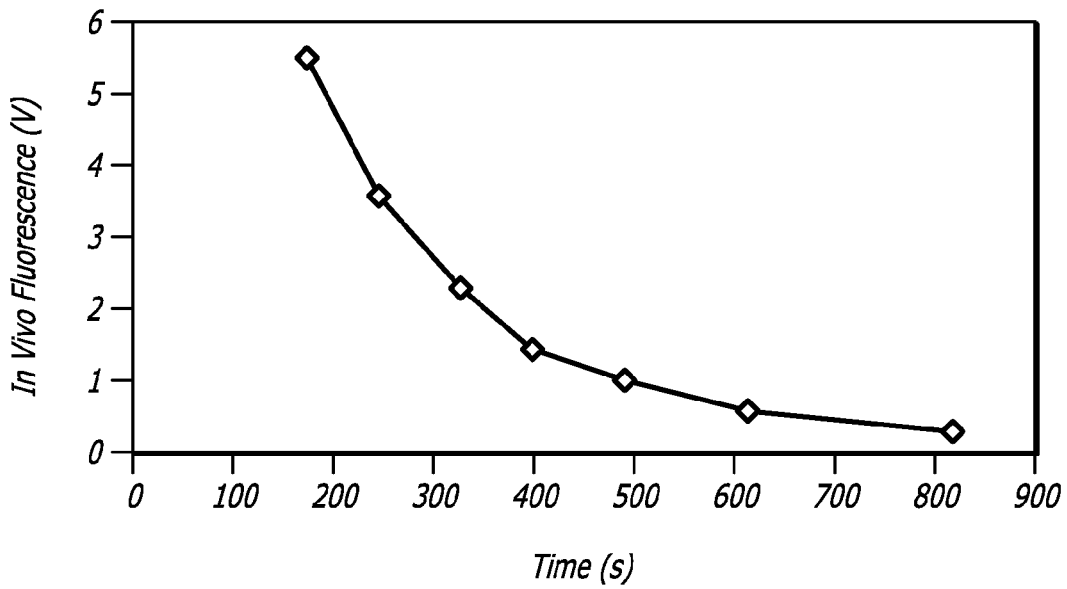
FIG. 5 is a depiction of a decay of fluorescence intensity curve as a function of time following injection of a 1 mg dose of indocyanine green (ICG) in an experimental animal.
Figure 6:
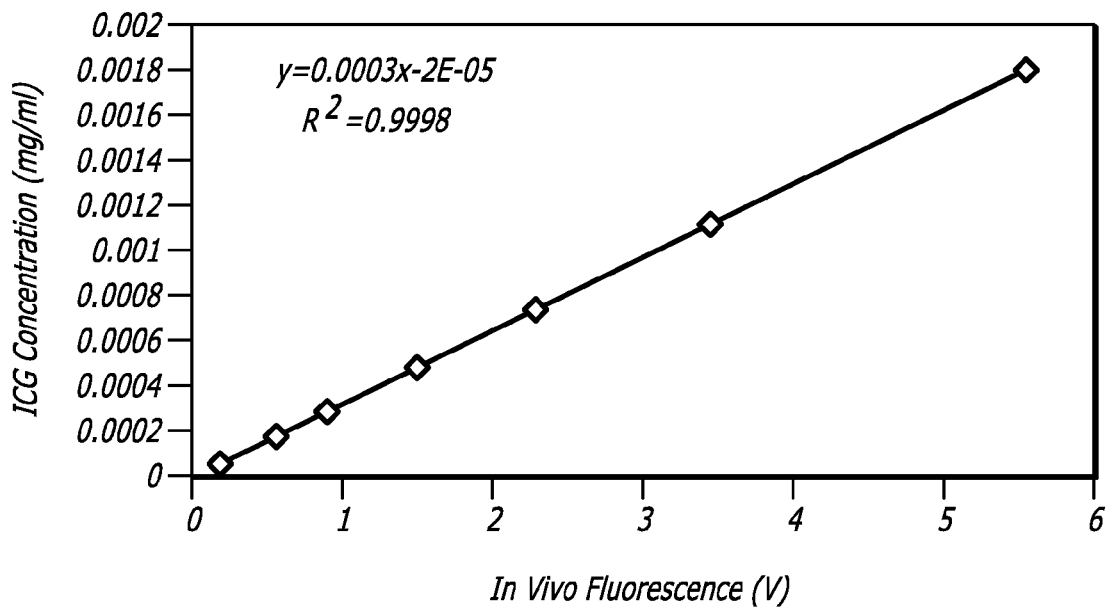
FIG. 6 is a depiction of a calibration curve for blood ICG concentration as a function of transcutaneous ICG fluorescence.

As shown in FIG. 5, the transcutaneous ear fluorescence intensity (in V) as a function of time (in s) after the high dose (1 mg) ICG injection during the calibration sequence. FIG. 5 shows the characteristic first order exponential decay of ICG in blood as the dye is being metabolized. FIG. 6 shows the ICG concentration (in mg/ml) as a function of the in vivo fluorescence for the same example and the same time points. For the range of concentrations used in these studies, ICG concentration and transcutaneous fluorescence were linearly related. The calibration line passes through the origin of the axes since there is no measured fluorescence when the ICG blood concentration is 0.

Thus, a simple proportionality factor exists between blood ICG concentration and transcutaneous fluorescence. This feature of the fluorescence dilution technique measuring light emission is advantageous over the conventional dye dilution technique based on ICG absorption which requires light absorption caused by ICG to be separated from light absorption by tissue and blood. After the proportionality factor is determined, ICG fluorescence dilution profiles can only then be converted into concentration measurements for computation of the cardiac output using the indicator-dilution equation.

Results of Cardiac Output Measurements.

Calibrated cardiac output readings have been obtained in 5 animals (body wt: 3.0±0.2 Kg). The following table lists the values during baseline conditions. The values are presented as the mean±standard deviation of three consecutive measurements obtained within a 15 min period.

TABLE 4

| Exp. | Cardiac output (ml/min) |
|---|---|
| 1 | 530 ± 15 |
| 2 | 500 ± 17 |
| 3 | 370 ± 12 |
| 4 | 434 ± 16 |
| 5 | 481 ± 6 |

The average for the five experiments (463 ml/min) is in order of reported cardiac outputs (260-675 ml/min) measured with ultrasound or thermodilution techniques in anesthetized rabbits (Preckel et al. Effect of dantrolene in an in vivo and in vitro model of myocardial reperfusion injury. Acta Anaesthesiol Scand, 44, 194-201, 2000. Fok et al. Oxygen consumption by lungs with acute and chronic injury in a rabbit model. Intensive Care Med, 27,1532-1538, 2001). Basal cardiac output varies greatly with experimental conditions such as type of anesthetic, duration and depth of anesthesia, leading to the wide range of values found in the literature. In this example, the variability (standard deviation/mean) of the calculated cardiac output with fluorescence dilution is ~3% for any triplicate set of measurements which compares favorably with the reported variability for the thermodilution technique (~5-10%).

C. Comparison of Measurements Obtained by Fluorescence Dilution Cardiac Output Method Via Transcutaneous Measurement and Subcutaneous Measurement.

Experimental Methodology.

The experimental preparation described in the preceding section (Example 2) includes two measurement sites for the fluorescence dilution traces: a transcutaneous site at the level of the ear central bundle of blood vessels and the exposed femoral artery. The ear vasculature is arterialized by local heating. With this preparation, the cardiac output estimates obtained from the peripheral non-invasive (transcutaneous) measurement site were compared with estimates obtained by interrogating a major artery.

The intensity of the fluorescence signal at the level of the exposed femoral artery during the slow metabolic disappearance phase of the injected ICG is compared to the calibrated ear fluorescence measurement to derive a calibration coefficient (arterial ICG fluorescence into ICG blood concentration). In this way cardiac output estimates expressed in ml/min were derived from the two sites.

Results.

Figure 8:
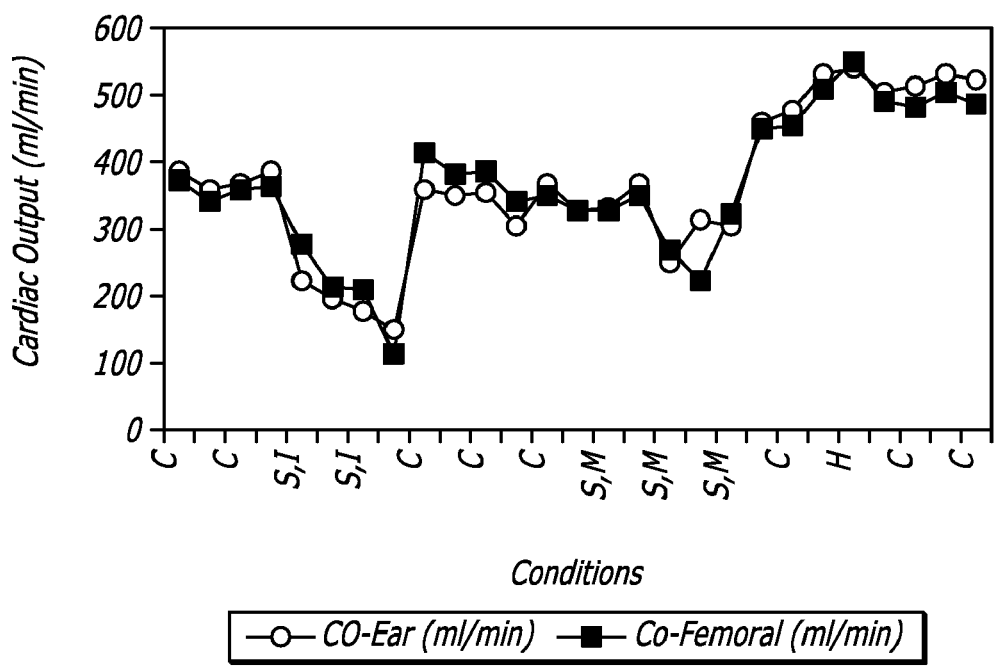
FIG. 8 is a depiction of cardiac output measurements derived from sites on the ear surface and on the exposed femoral artery during one experiment.

FIG. 8 shows the time course of the cardiac output measurements obtained from the ear site and from the exposed femoral artery in a representative experiment during control conditions (C), intense then mild vagal stimulation (S,I and S,M), and post-stimulation hyperemia (H). Near-identical estimates of the cardiac output are obtained from the two sites during all phases of the study.

The relationship between cardiac output derived from measurement of the fluorescence dilution curve at the level of the skin surface ($Co_{skin}$, in ml/min) and at the level of the exposed femoral artery ($Co_{fem}$, in ml/min) was investigated. The linear relationships between the two measures are summarized in the table below:

TABLE 5

| Exp. | Linear regression | Regression Coefficient. | Number measurements |
|---|---|---|---|
| 1 | $Co_{skin} = 0.65(\pm 0.11) * Co_{fem} + 145.0(\pm 54.0)$ | 0.81 | 22 |
| 2 | $Co_{skin} = 1.01(\pm 0.06) * Co_{fem} + 2.0(\pm 22.0)$ | 0.96 | 27 |
| 3 | $Co_{skin} = 1.05(\pm 0.14) * Co_{fem} - 56.0(\pm 54.0)$ | 0.91 | 13 |

The two measures of fluorescence cardiac output are tightly correlated. In the last two experiments, the slope of the regression line is not statistically different from 1.0 and the ordinate is not different from 0.0 indicating that the two measurements are identical. These observations suggest that fluorescence dilution cardiac output can be reliably measured transcutaneously and from a peripheral site of measurement that has been arterialized by local application of heat. Attenuation of the excitation light and ICG fluorescence emission by the skin does not prevent the measurement of well-defined dye dilution traces that can be analyzed to derive the cardiac output.

D. Comparison of Measurements Obtained by Fluorescence Dilution Cardiac Output Method and Doppler Flow Velocity Technique.

Experimental Methodology.

The present method was compared with an ultrasonic Doppler velocity probe method to record cardiac output measurements. In this example the above procedure was modified in that, the animal's chest was opened with a median incision of the sternum and a 6 mm 20 MHz Doppler velocity probe was gently passed around the ascending aorta and tightened into a loop that fits snuggly around the aorta.

For detection of the fluorescent detection of the indicator, two illumination+detection fiber optic probes were used: one probe was placed on or above the ear middle vessel bundle and the other probe was placed in proximity to the dissected left femoral artery. Local heating to 42 degrees centigrade arterialized the ear vasculature.

Figure 7:
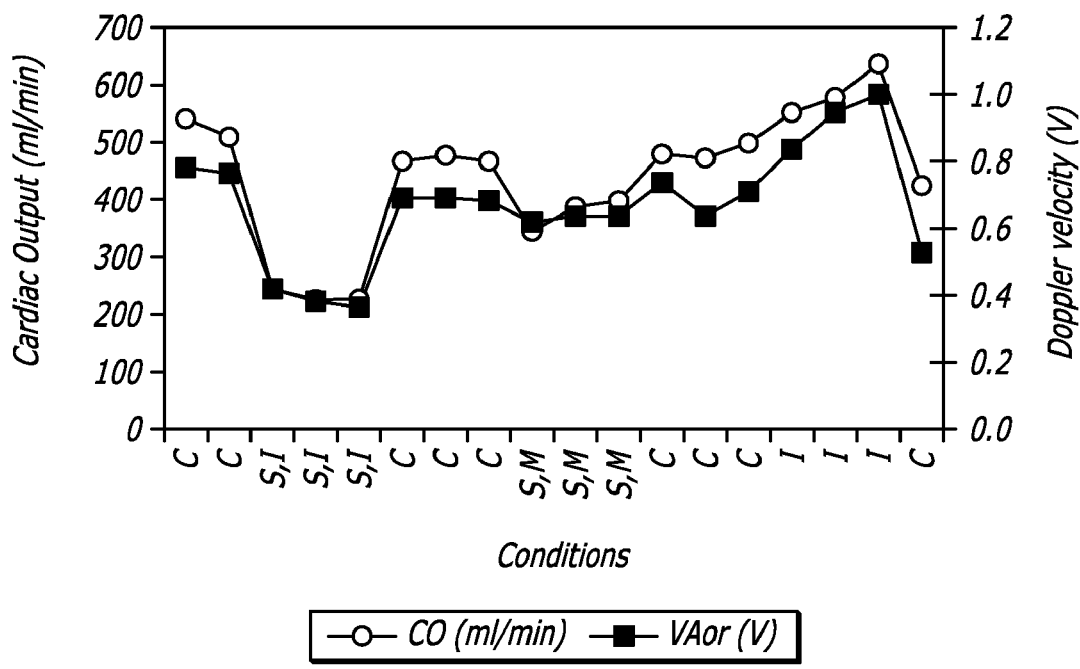
FIG. 7 is a depiction of cardiac output and aortic velocity measurements during one representative experiment.

In this example, two maneuvers were used to change the cardiac output from its control level: vagal stimulation, which reduces the cardiac output, and saline infusion, which increases the circulating volume and cardiac output. The right vagal nerve was dissected to position a stimulating electrode. Stimulation of the distal vagus results in a more or less intense decrease of the heart rate that depends on the stimulation frequency and voltage (1 ms pulses, 3 to 6 V, 10 to 30 Hz). The cardiac output and aortic flow velocity also decrease during vagal stimulation even though less markedly than the heart rate decreases because the stroke volume increases. Saline infusion at a rate of 15-20 ml/min markedly increases the cardiac output. FIG. 7 shows the time course of the cardiac output and aortic velocity measurements in one experiment including control conditions (C), intense then mild vagal stimulation (S,I and S,M), and saline infusion (I).

Results.

There is consistent tracking of the Doppler aortic velocity by the fluorescence dilution cardiac output measurement. The relationship between fluorescence dilution cardiac output and aortic Doppler flow velocity was investigated in four rabbits.

The linear relationships between fluorescence dilution cardiac output (CO, in ml/min) and aortic flow velocity signal (vAor, not calibrated, in Volts) are summarized in the table:

TABLE 6

| Exp. | Linear regression | Regression Coefficient | Measurements |
|------|-------------------|------------------------|--------------|
| 1 | CO = 789(±123) * VAor + 166(±34) | 0.79 | 27 |
| 2 | CO = 607(±62) * Vaor + 50(±32) | 0.90 | 24 |
| 3 | CO = 614(±64) * Vaor − 45(±38) | 0.90 | 27 |
| 4 | CO = 654(±41) * Vaor − 3(±29) | 0.97 | 18 |

This data indicates that the fluorescence dilution cardiac output is highly correlated with aortic flow velocity as indicated by the elevated regression coefficient ($\geq 0.9$ in 3 experiments). Further, the slopes of the linear regression lines between fluorescence dilution cardiac output and aortic flow velocity are similar and statistically not different in the four studies. This suggests a constant relationship between the two variables across experiments. The ordinates of regression lines are not different from 0 in the last three experimental studies, which suggests absence of bias between the two measures of aortic flow.

The results above establish that fluorescence dilution cardiac output measured transcutaneously tracks the Doppler flow velocity measured in the ascending aorta.

Example 3

Comparison with Thermodilution Method

Experimental methodology. Other experiments were performed in New Zealand White rabbits using the methodology described for the preceding example 2. In addition, a 4F thermodilution balloon catheter was inserted into the right femoral vein and advanced until the thermistor reached the main pulmonary artery. Correct placement of the catheter tip was verified visually through the thoracotomy. The catheter was connected to a cardiac output computer to measure the thermodilution cardiac output. Cardiac output measurements were obtained with the present method ($CO_{ICG}$) and the comparison thermodilution method ($CO_{TD}$) during baseline conditions, reduced flow conditions resulting from vagal stimulation, and increased flow conditions resulting from blood volume expansion with saline.

Results.

Average values of $CO_{ICG}$ and $CO_{TD}$ measured in baseline conditions in the 10 animals were 412 (±13) ml/min and 366 (±11) ml/min, respectively, in the expected range for anesthetized rabbits. In each animal, $CO_{ICG}$ was linearly related to $CO_{TD}$ as shown on the following table 7. The slope of the regression line (range: 0.74-1.25) was not different from 1.0 in 8 studies. In the combined data from all 10 studies the linear relationship between $CO_{ICG}$ and $CO_{TD}$ had a slope (0.95±0.03) not different from 1.0 and an ordinate (77±10 ml/min) that was slightly >0.

TABLE 7

| Experiment | EQUATION | N | R |
|------------|----------|---|---|
| 1 | $CO_{ICG} = 0.94^\dagger(\pm 0.08) CO_{TD} + 84(\pm 23)$ | 21 | 0.94 |
| 2 | $CO_{ICG} = 1.25^\dagger(\pm 0.17) CO_{TD} - 0^*(\pm 39)$ | 17 | 0.88 |
| 3 | $CO_{ICG} = 0.74^\dagger(\pm 0.11) CO_{TD} + 122(\pm 26)$ | 20 | 0.85 |
| 4 | $CO_{ICG} = 0.90^\dagger(\pm 0.05) CO_{TD} + 98(\pm 15)$ | 11 | 0.99 |
| 5 | $CO_{ICG} = 1.08^\dagger(\pm 0.11) CO_{TD} + 84(\pm 47)$ | 14 | 0.94 |
| 6 | $CO_{ICG} = 1.07^\dagger(\pm 0.09) CO_{TD} + 16^*(\pm 33)$ | 14 | 0.96 |
| 7 | $CO_{ICG} = 1.15(\pm 0.06) CO_{TD} + 29^*(\pm 25)$ | 12 | 0.99 |
| 8 | $CO_{ICG} = 0.82^\dagger(\pm 0.09) CO_{TD} + 83(\pm 37)$ | 12 | 0.94 |
| 9 | $CO_{ICG} = 0.88^\dagger(\pm 0.12) CO_{TD} + 98^*(\pm 62)$ | 16 | 0.89 |
| 10 | $CO_{ICG} = 1.05^\dagger(\pm 0.08) CO_{TD} - 20^*(\pm 33)$ | 15 | 0.97 |
| All | $CO_{ICG} = 0.95^\dagger(\pm 0.03) CO_{TD} + 74(\pm 10)$ | 152 | 0.94 |

These studies further established that cardiac output $CO_{ICG}$ measured with the present method is linearly related to thermodilution cardiac output $CO_{TD}$. The slope of the regression line between these variables was near 1.0 for most experiments, as well as for the grouped data from all experiments.

Example 4

A. Noninvasive Calibration

One embodiment of the calibration system includes a method to determine non-invasively transcutaneously the concentration of a fluorescent indicator injected in the bloodstream by measuring the intensity of the fluorescence light emitted by the indicator when illuminated by a light source in or near the skin and the intensity of the light from that source reflected by or transmitted through the illuminated skin site.

In the pulse dye densitometer (Cardiac output and circulating blood volume analysis by pulse dye densitometry. Iijima T. et al. Journal of Clinical Monitoring, 13, 81-89, 1997, incorporated herein in its entirety by reference), light absorption is measured at two wavelengths: 805 nm where ICG absorption is near maximum and 890 nm where ICG absorption is very small. Assuming at first that tissue absorption of light is only due to blood hemoglobin and ICG, the ratio $C_{ICG}/C_{Hb}$ can be expressed as a function of the ratio $\psi$ of the optical densities measured at 805 nm and 890 nm, $$C_{ICG}/C_{Hb} = \frac{E_{Hb,805} - \Psi E_{Hb,890}}{\Psi E_{ICG,890} - E_{ICG,805}}$$

where E represents the absorption coefficient from Beer's Law. The latter is expressed as $I_x = I_0 \, e^{-E \cdot C \cdot x}$ with C=concentration, E=absorption coefficient, x=path length in substance. Note that if we assume that $E_{ICG,890}=0$, the ratio of the concentrations $C_{ICG}/C_{Hb}$ is linearly related to the ratio of the optical densities measured at two wavelengths.

Taking into account scattering and absorption by other material beside ICG and Hb, the developers of the pulse dye densitometer established that the ratio of the optical density changes between before and after ICG administration at 805 nm and 890 nm could be expressed as a function of the ratio $C_{ICG}/C_{Hb}$.

ICG fluorescence is proportional to the absorption of light by ICG at the wavelength of excitation (805 nm in the model above or 784 nm in our studies). Therefore, we hypothesized that the ratio $C_{ICG}/C_{Hb}$ can be derived from the ratio of the change in light signal measured at the wavelength of emission (related to ICG fluorescence) to the light signal measured at the wavelength of excitation (related to ICG and Hb absorption).

We considered a model of light propagation in tissue, which at first assumed that only hemoglobin and ICG were absorbers (See Table 8 below). The absorption coefficients of ICG and Hb were derived from the literature and considered to be independent of wavelength. We then added a dependence of the absorption coefficients on wavelength and tissue absorption in the model to investigate the effect of these factors.

globin contents when absorption coefficients are the same, and the results are illustrated in the graphs of FIGS. 11A-11D. For this simple model, the transmitted excitation light decreases nonlinearly as a function of ICG concentration in the model and the curve varies with the hemoglobin content

TABLE 8

1-D MODEL OF LIGHT PROPAGATION AND FLUORESCENCE GENERATION

| $\boxed{X}$ | $\Delta_X$ | | $\Delta_X$ |
|---|---|---|---|
| | Excitation absorbed Hb $I_0\mu_{a,Hb}C_{Hb}\Delta_X$ | | Excitation absorbed Hb $I_1\mu_{a,Hb}C_{Hb}\Delta_X$ |
| Incident $I_0$ | Excitation absorbed ICG $I_0\mu_{a,ICG}C_{ICG}\Delta_X$ | Excitation transmitted total $I_1 = I_0 - I_0(\mu_{a,Hb}C_{Hb}+\mu_{a,ICG}C_{ICG})\Delta_X$ | Excitation absorbed ICG $I_1\mu_{a,ICG}C_{ICG}\Delta_X$ |
| | Excitation absorbed total $I_0(\mu_{a,Hb}C_{Hb}+\mu_{a,ICG}C_{ICG})\Delta_X$ | | Excitation absorbed total $I_1(\mu_{a,Hb}C_{Hb}+\mu_{a,ICG}C_{ICG})\Delta_X$ |
| | Fluorescence produced ICG $Q \cdot I_0\mu_{a,ICG}C_{ICG}\Delta_X$ | Fluo. transmitted total $F_1 = Q \cdot I_0\mu_{a,ICG}C_{ICG}\Delta_X$ | Fluorescence produced ICG $Q \cdot I_1\mu_{a,ICG}C_{ICG}\Delta_X$ |
| $F_0 = 0$ | Fluorescence absorbed Hb 0 | | Fluorescence absorbed Hb $F_1\mu_{a,Hb}C_{Hb}\Delta_X$ |
| | Fluorescence absorbed ICG 0 | | Fluorescence absorbed ICG $F_1\mu_{a,ICG}C_{ICG}\Delta_X$ |
| | Fluorescence absorbed total 0 | | Fluorescence absorbed total $F_1(\mu_{a,Hb}C_{Hb}+\mu_{a,ICG}C_{ICG})\Delta_X$ |

| $\boxed{X}$ | | $\Delta_X$ | |
|---|---|---|---|
| | | Excitation absorbed Hb $I_2\mu_{a,Hb}C_{Hb}\Delta_X$ | |
| | Excitation transmitted total $I_2 = I_1 - I_1(\mu_{a,Hb}C_{Hb}+\mu_{a,ICG}C_{ICG})\Delta_X$ | Excitation absorbed ICG $I_2\mu_{a,ICG}C_{ICG}\Delta_X$ | |
| | | Excitation absorbed total $I_2(\mu_{a,Hb}C_{Hb}+\mu_{a,ICG}C_{ICG})\Delta_X$ | |
| | Fluo. transmitted total | Fluorescence produced ICG $Q \cdot I_2\mu_{a,ICG}C_{ICG}\Delta_X$ | ... |
| | $F_2 = Q \cdot I_1\mu_{a,ICG}C_{ICG}\Delta_X - F_1(\mu_{a,Hb}C_{Hb}+\mu_{a,ICG}C_{ICG})\Delta_X$ | Fluorescence absorbed Hb $F_2\mu_{a,Hb}C_{Hb}\Delta_X$ | |
| | | Fluorescence absorbed ICG $F_2\mu_{a,ICG}C_{ICG}\Delta_X$ | |
| | | Fluorescence absorbed total $F_2(\mu_{a,Hb}C_{Hb}+\mu_{a,ICG}C_{ICG})\Delta_X$ | |

The following data and assumptions were applied to the model of Table 8:

$\mu_{a,ICG} = a_{ICG} = 38.1 \, \mu l \cdot \mu g^{-1} \cdot mm^{-1}$ for wavelength $\lambda = 784$ nm $\mu_{a,HbO2} \sim \mu_{a,Hb} = 0.0026 \, \mu l \cdot \mu g^{-1} \cdot mm^{-1}$ for wavelength $\lambda = 784$ nm Initially, we assume that the absorption coefficients have the same values at 830 nm (fluorescence) and at 784 nm (incident excitation light).

Figure 11A:
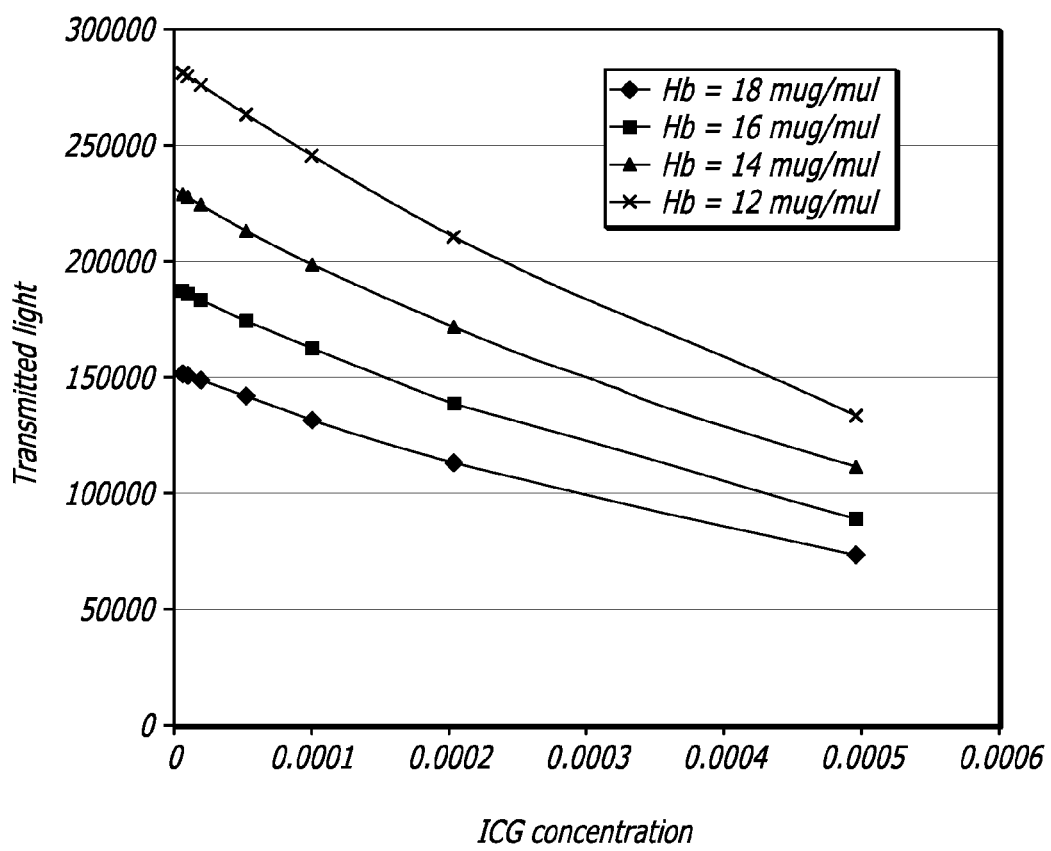
FIGS. 11A-11D are graphs showing calculated transmission and fluorescence signals at 784 nm and 830 nm for different ICG concentrations and hemoglobin contents when absorption coefficients are the same at these two wavelengths.
Figure 11B:
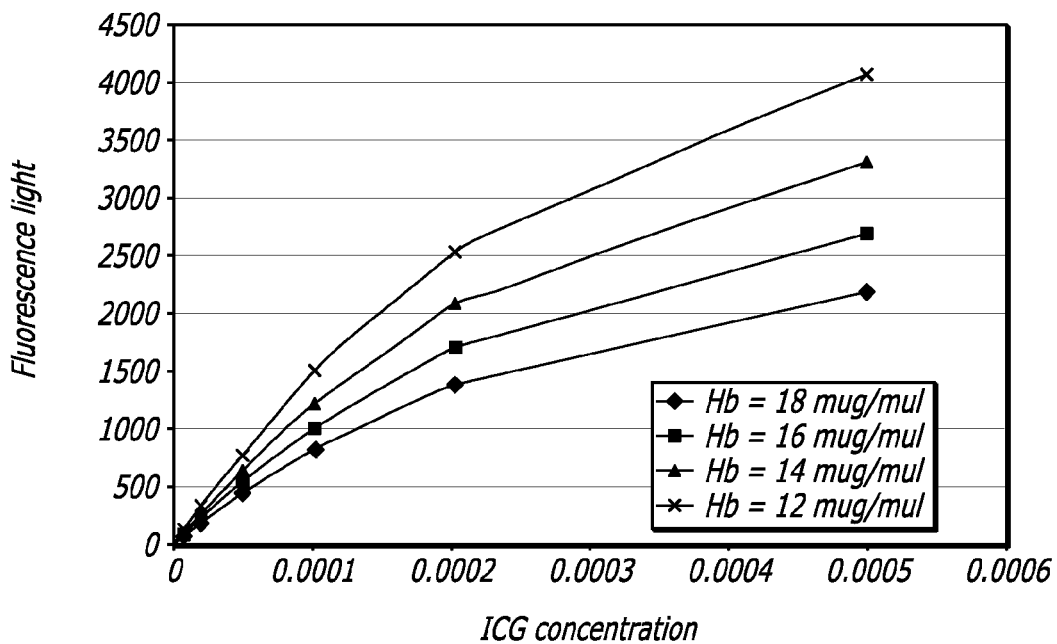
Figure 11C:
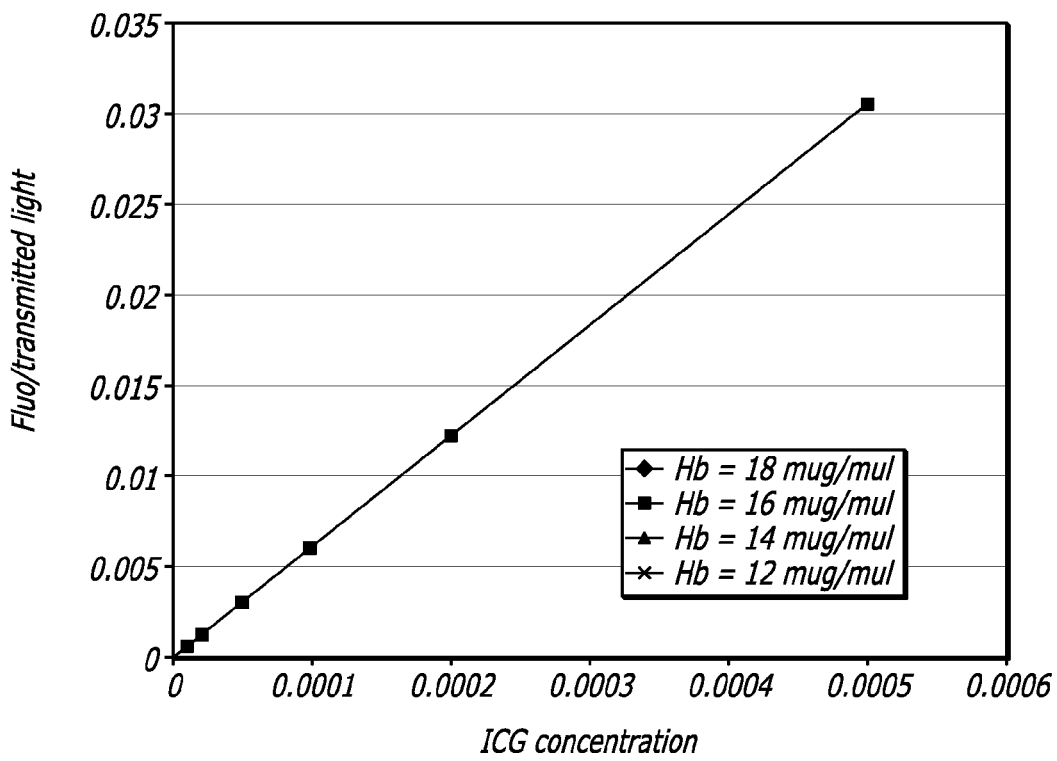
Figure 11D:
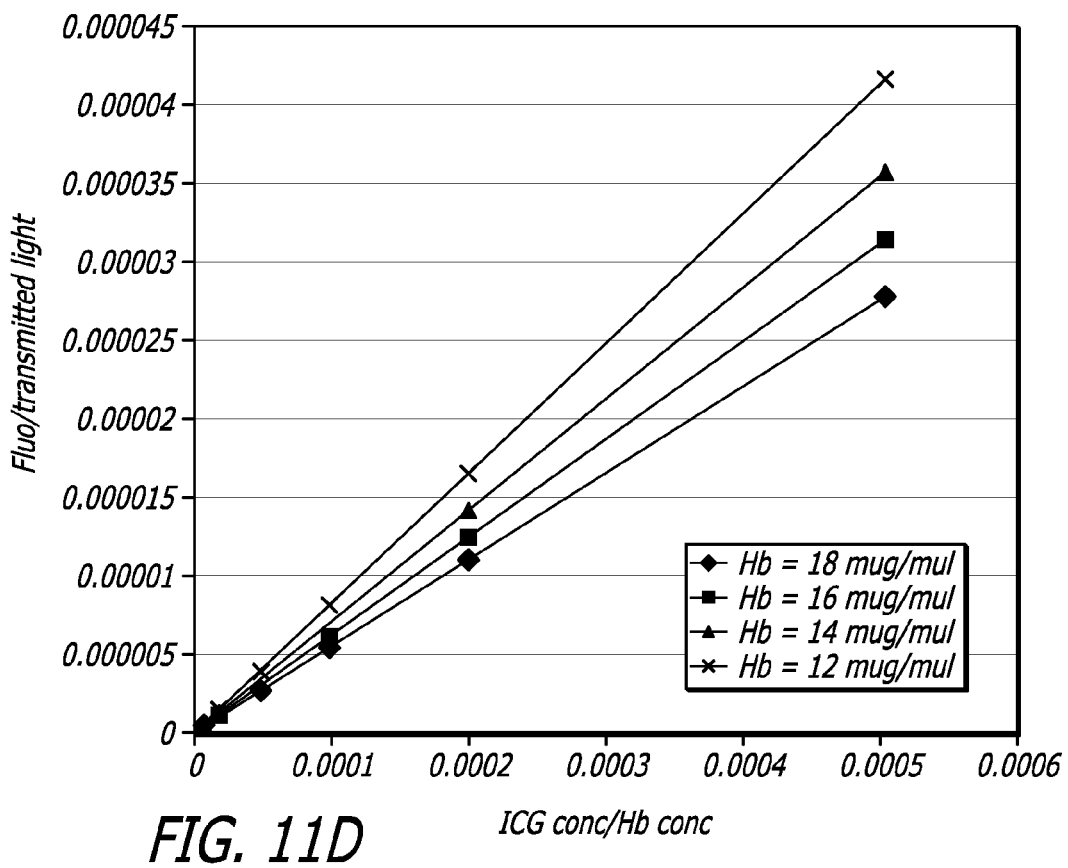

$C_{Hb} = 12-18 \, g \cdot dl^{-1} = 120-180 \, \mu g/\mu l$ in blood $C_{ICG}$ max = 0.005 μg/μl in blood Tissue assumed to contain 10% blood
Quantum yield of ICG fluorescence=0.04
Transmission calculated through 40 mm tissue in 0.02 mm increment We modeled transmission and fluorescence signals at 784 nm and 830 nm for different ICG concentrations and hemo- (see FIG. 11A). Also the emergent fluorescence light nonlinearly increases with ICG concentration (inner filter effect) and the curve varies with hemoglobin content (see FIG. 11B). Thus, the fluorescence signal varies markedly if there is more or less absorption by blood in the tissue.

However, the ratio (emergent fluorescence light/transmitted excitation light) is proportional to the ICG concentration and independent of the hemoglobin content of the tissue (see FIG. 11C). Therefore, by measuring the ratio and if the relationship is known, the ICG concentration can be estimated. Also, the ratio (emergent fluorescence light/transmitted excitation light) is proportional to the ratio (ICG concentration/Hb concentration) but in this case the slope varies with the hemoglobin content of the tissue (see FIG. 11D). In an alternative embodiment of the calibration system, the concentration of Hb may be obtained from a blood sample, and this concentration value can be used to determine the ratio of ICG value to Hb value, which can then be used with the ratio of transmitted excitation light to fluorescence light to determine the concentration of ICG for calibration.

We also modeled transmission and fluorescence signals and at 784 nm and 830 nm for different ICG concentrations and hemoglobin contents when absorption coefficients are the different and an additional absorber is included, and the results are illustrated in the graphs of FIGS. 12A-12D.

Absorption by ICG is actually slightly more elevated at 784 nm (excitation) than it is at 830 nm (fluorescence peak). In contrast oxy-hemoglobin absorption is less at 784 nm (excitation) than it is at 830 nm. In addition to blood hemoglobin and ICG, bloodless tissue absorbs to a certain extent. We determined various values from the literature:

$\mu_{a,ICG}=38.1 \; \mu l \cdot \mu g^{-1} \cdot mm^{-1}$ for wavelength $\lambda=784$ nm
$\mu_{a,HbO2} \sim \mu_{a,Hb}=0.0026 \; \mu l \cdot \mu_g^{-1} \cdot mm^{-1}$ for wavelength $\lambda=784$ nm
$\mu_{a,ICG}=34.1 \; \mu l \cdot \mu_g^{-1} \cdot mm^{-1}$ for wavelength $\lambda=830$ nm
$\mu_{a,HbO2} \sim \mu_{a,Hb}=0.0035 \; \mu l \cdot \mu_g^{-1} \cdot mm^{-1}$ for wavelength $\lambda=830$ nm
$\mu_{a,tissue}=0.1 \cdot mm^{-1}$ independent of wavelength in the range 784-830 nm.

$C_{Hb}=12-18 \; g \cdot dl^{-1}=120-180 \; \mu g/\mu l$ in blood
$C_{ICG}$ max=0.005 $\mu g/\mu l$ in blood
Tissue assumed to contain 10% blood
Quantum yield of ICG fluorescence=0.04
Transmission calculated through 40 mm tissue in 0.02 mm increment For this more complete model, the magnitude of the transmitted excitation light and emergent fluorescent lights are markedly decreased when compared to the first model primarily because of the absorption by bloodless tissue. Both signals follow the pattern found for the simple model. In particular, the emergent fluorescence light nonlinearly increases with ICG concentration (inner filter effect) and the curve varies with hemoglobin content.

Figure 12A:
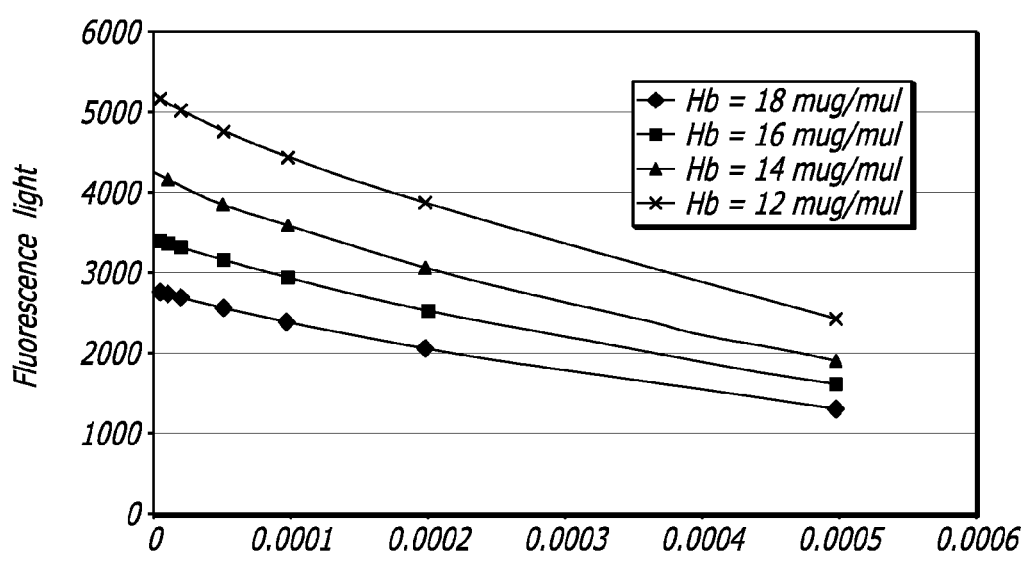
FIGS. 12A-12D are graphs showing transmission and fluorescence signals at 784 nm and 830 nm for different ICG concentrations and hemoglobin contents when absorption coefficients vary with wavelength and an additional absorber is included.
Figure 12B:
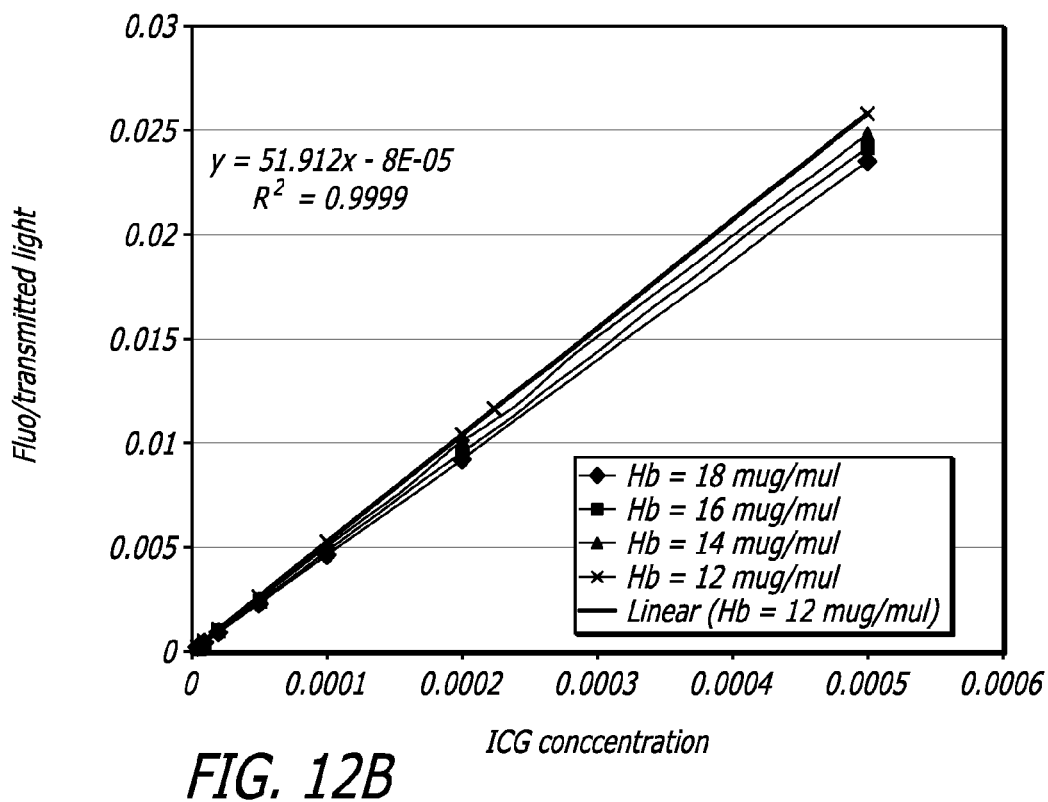
Figure 12C:
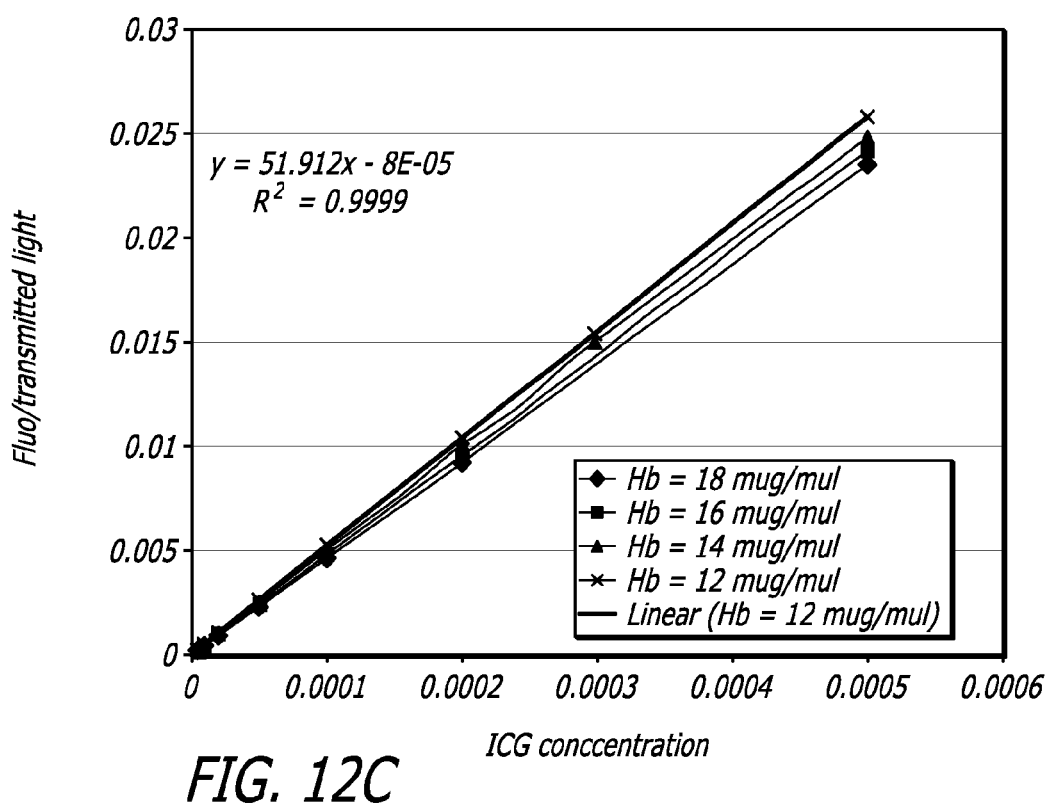
Figure 12D:
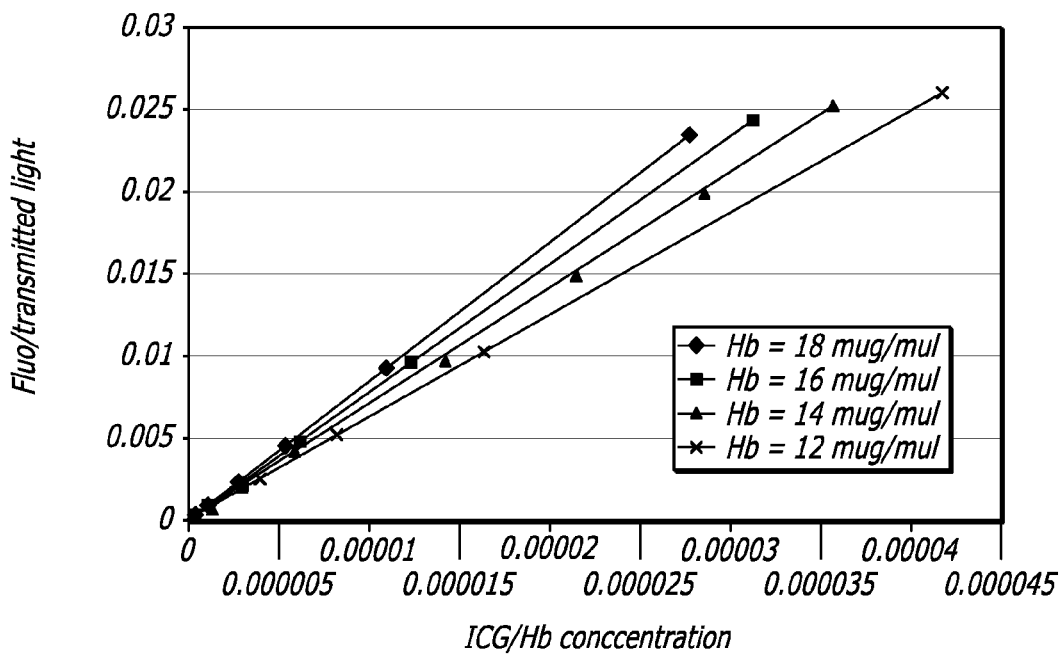

As before the ratio (emergent fluorescence light/transmitted excitation light) is proportional to the ICG concentration (See FIG. 12C). While the slope is dependent on the hemoglobin content, there are only small differences between the four levels of hemoglobin considered. This suggests that by measuring the ratio of the fluorescence/transmitted light, the ICG concentration can be estimated once the linear relationship is determined and possibly including a factor that accounts for the hemoglobin content.

While these models do not consider tissue scattering, the latter is often assumed to increase the path length of light in tissue by a fixed proportionality factor: the path length factor (about 3.6 for human forearm, see Measurement of hemoglobin flow and blood flow by near-infrared spectroscopy. Edwards A. D. et al.—J. Appl. Physiol. 75, 1884-1889, 1993, the entire contents of which are incorporated herein by reference). This suggests that the model analysis above would likely remain valid even in the presence of scattering.

The previous description of the disclosed embodiments is provided to enable any person skilled in the art to make or use the cardiac output monitor devices, methods and systems. Various modifications to these embodiments will be readily apparent to those skilled in the art, and the generic principles defined herein may be applied to other embodiments without departing from the spirit or scope of the devices, methods and systems described herein. Thus, the cardiac output, devices, methods and systems are not intended to be limited to the embodiments shown herein but are to be accorded the widest scope consistent with the principles and novel features disclosed herein.

The invention claimed is:

1. A system for determining non-invasively at least one cardiovascular parameter of a patient undergoing hemodialysis comprising:

a) a dialyzer configured to perform hemodialysis on the patient, wherein the hemodialysis comprises blood removal from and administration of a fluorescent dye to the cardiovascular system of the patient;
b) a probe assembly comprising:
 i) an optical illumination source configured to illuminate the removed blood having the administered fluorescent dye with a first wavelength of light, wherein the illumination causes the fluorescent dye to emit light of a second wavelength, wherein the second wavelength is different than the first wavelength; and
 ii) at least one optical detector configured to detect the intensity of light, having the second wavelength, that is emitted from the illuminated fluorescent dye, and configured to send a corresponding electronic signal;
c) a processor configured to receive the sent electronic signal and to estimate at least one cardiovascular parameter of the patient based on the sent electronic signal; wherein the processor is configured to correct the estimation of the at least one cardiovascular parameter for changes in the blood hematocrit or hemoglobin content of the patient undergoing hemodialysis; and
d) a monitoring system configured to monitor the estimated cardiovascular parameter during hemodialysis.

2. The system of claim 1, wherein the administered fluorescent dye is indocyanine green (ICG).

3. The system of claim 2, wherein the probe further comprises a plurality of optical detectors that are configured to detect plurality of light intensities having the same or different wavelengths.

4. The system of claim 3, wherein the processor is further configured to determine the ICG concentration.

5. The system of claim 3, wherein the processor is configured to determine the ICG concentration based on combined relationships:

$$C_{ICG}=A \cdot T^\alpha \cdot B_{Fluo} \text{ and } C_{ICG}=K \cdot R^\gamma \cdot B_{Fluo}$$

where $C_{ICG}$ is the blood ICG concentration, $B_{Fluo}$ represents the back-fluorescence intensity having the second wavelength, T and R being the transmitted and reflected lights, respectively, having the first wavelength and parameters A, K, $\alpha$ and $\gamma$ are predetermined constants.

6. The system of claim 4, wherein the processor is configured to determine the ICG concentration based on a relationship:

$$C_{ICG}=A \cdot T^\alpha \cdot B_{Fluo}$$

where $C_{ICG}$ is the blood ICG concentration, $B_{Fluo}$ represents the back-fluorescence intensity having the second wavelength, T is the transmitted light intensity having the first wavelength, and parameters A and $\alpha$ are predetermined constants.

7. The system of claim 4, wherein the processor is configured to determine the ICG concentration based on a relationship:

$$C_{ICG}=B \cdot T^\beta \cdot F_{Fluo}$$

where $C_{ICG}$ is the blood ICG concentration, $F_{Fluo}$ represents the forward-fluorescence intensity having the second wavelength, T is the transmitted light intensity having the first wavelength and parameters B and $\beta$ are predetermined constants.

8. The system of claim 4, wherein the processor is configured to perform a computation using the following relationship to determine the ICG concentration:

$$C_{ICG}=K \cdot R^\gamma \cdot B_{Fluo}$$

where $C_{ICG}$ is the blood ICG concentration, $B_{Fluo}$ is the back-fluorescence intensity having the second wavelength, R is the reflected light intensity having the first wavelength and the exponent γ and parameter K being predetermined constants.

9. The system of claim 4, wherein the processor is configured to determine the ICG concentration based on a relationship:

$$C_{ICG}=K \cdot R^\gamma \cdot F^{Fluo}$$

where $C_{ICG}$ is the blood ICG concentration, $F_{Fluo}$ represents the forward-fluorescence intensity having the second wavelength, R is the reflected light intensity having the first wavelength, and parameters K and γ are predetermined constants.

10. The system of claim 4, wherein the processor is configured to determine the ICG concentration based on combined relationships: $C_{ICG}=B \cdot T^\beta \cdot F_{Fluo}$ and $C_{ICG}=K \cdot R^\gamma \cdot F_{Fluo}$ where $C_{ICG}$ is the blood ICG concentration, $F_{Fluo}$ represents the forward-fluorescence intensity having the second wavelength, T and R are the transmitted and the reflected light intensities having a wavelength different than the second wavelength and the parameters B, K, β and γ are predetermined constants.

11. The system of claim 1, wherein the fluorescent dye is administered through inserting a fine catheter at any of peripheral vein, the arterio-venous (AV) fistula or the arterio-venous (AV) shunt.

12. The system of claim 1, wherein the dialyzer further comprises a transparent tubing configured to remove blood from the patient to the dialyzer, and wherein the probe is configured to be attached to the external wall of the tubing.

13. The system of claim 1, wherein the probe further comprises a second optical detector configured to detect a light intensity having the first wavelength.

14. The system of claim 13, wherein the second optical detector is configured to detect one of the reflected or transmitted light that is emitted from the removed blood.

15. The system of claim 1, wherein the optical detector is configured to detect one of the back-fluorescence or forward-fluorescence that is emitted by the fluorescent dye.

16. The system of claim 1, wherein the probe is pre-calibrated.

17. The system of claim 1, wherein the probe is calibrated non-invasively and in-vitro.

18. The system of claim 1, wherein the dialyzer further comprises a side port configured to return the dialyzed blood to the patient, and wherein the fluorescent dye is administered through the side port into the cardiovascular system of the patient.

19. The system of claim 1, wherein the at least one cardiovascular parameter is cardiac output and circulating blood volume.

20. The system of claim 1, wherein the cardiovascular parameter is cardiac output.

21. The system of claim 20, wherein the processor is further configured to estimate the cardiac output through a dilution curve.

22. The system of claim 1, wherein the cardiovascular parameter is circulating blood volume.

23. The system of claim 22, wherein the processor is further configured to estimate the circulating blood volume through subtracting the removed blood volume in the dialyzer's compartment from the total circulating blood volume of the patient.

24. The system of claim 1, wherein the monitoring system is further configured to adjust the rate of the blood removal from the patient when the estimated cardiac output and/or the circulating blood volume changes.

* * * * *